(12) United States Patent
Seki et al.

(10) Patent No.: US 8,943,658 B2
(45) Date of Patent: Feb. 3, 2015

(54) MANUFACTURING APPARATUS AND MANUFACTURING METHOD OF TAMPON

(75) Inventors: Shinobu Seki, Kagawa (JP); Hideki Onishi, Kagawa (JP); Masashi Hosokawa, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 647 days.

(21) Appl. No.: 13/119,981

(22) PCT Filed: Sep. 17, 2009

(86) PCT No.: PCT/JP2009/066228
§ 371 (c)(1),
(2), (4) Date: May 12, 2011

(87) PCT Pub. No.: WO2010/035677
PCT Pub. Date: Apr. 1, 2010

(65) Prior Publication Data
US 2011/0209317 A1    Sep. 1, 2011

(30) Foreign Application Priority Data

Sep. 29, 2008  (JP) .................................. 2008-251448

(51) Int. Cl.
*B65H 29/00*  (2006.01)
*B29C 65/00*  (2006.01)
(Continued)

(52) U.S. Cl.
CPC ........... *A61F 13/263* (2013.01); *A61F 13/2097* (2013.01)
USPC .................. 28/118; 29/235; 29/446; 29/450; 29/525; 29/700; 156/556; 156/566

(58) Field of Classification Search
USPC ........... 29/235, 244, 271, 446, 450, 451, 525, 29/525.01, 700; 28/118; 156/556, 566, 156/443
See application file for complete search history.

(56) References Cited

U.S. PATENT DOCUMENTS 2,263,909 A * 11/1941 Webb ............................... 28/120
3,683,759 A *  8/1972 Voss et al. ...................... 493/231
(Continued)

FOREIGN PATENT DOCUMENTS

AU         2353192      4/1993
CN      101155568 A     4/2008
(Continued)

OTHER PUBLICATIONS

Japanese Office Action for Application No. 2008-251448 mailed Oct. 30, 2012.
(Continued)

*Primary Examiner* — Essama Omgba
*Assistant Examiner* — Darrell C Ford
(74) *Attorney, Agent, or Firm* — Lowe Hauptman & Ham LLP

(57) ABSTRACT

An apparatus for manufacturing a tampon includes a pushing-member inserting mechanism that inserts a pushing member into an accommodating cylinder through a leading-end opening; and a tampon main body inserting mechanism that inserts a tampon main body into the accommodating cylinder from side including a cord through the leading-end opening; a drive section connecting the guide tube and the accommodating cylinder by moving one of the guide tube and the accommodating cylinder towards other one and thus contacting the guide tube and the leading-end part of the accommodating cylinder; a pressing part pressing the tampon main body inserted into the guide tube so as to insert the tampon main body into the accommodating cylinder connected to the guide tube; and an air suction device sucking air from rear-end side of the accommodating cylinder in a case where the tampon main body is inserted into the accommodating cylinder.

13 Claims, 15 Drawing Sheets

(51) Int. Cl.
*B23P 19/00* (2006.01)
*B23P 19/02* (2006.01)
*A61F 13/26* (2006.01)
*A61F 13/20* (2006.01)

(56) References Cited

U.S. PATENT DOCUMENTS

| | | | | |
|---|---|---|---|---|
| 4,104,013 | A * | 8/1978 | Kelly et al. | 425/324.1 |
| 4,321,933 | A | 3/1982 | Baessler | |
| 4,321,993 | A * | 3/1982 | Hinzmann et al. | 198/400 |
| 4,411,647 | A * | 10/1983 | Sakurai et al. | 604/16 |
| 5,165,152 | A * | 11/1992 | Kramer et al. | 28/118 |
| 5,389,067 | A * | 2/1995 | Rejai | 604/14 |
| 5,575,047 | A * | 11/1996 | Gerstenberger et al. | 28/119 |
| 6,056,714 | A * | 5/2000 | McNelis et al. | 604/14 |
| 6,248,089 | B1 * | 6/2001 | Porat | 604/17 |
| 2005/0145342 | A1 * | 7/2005 | Murray | 156/556 |
| 2008/0110005 | A1 * | 5/2008 | Gilbert et al. | 28/118 |
| 2008/0210067 | A1 * | 9/2008 | Schlinz et al. | 83/23 |
| 2009/0260205 | A1 * | 10/2009 | Binner et al. | 28/118 |

FOREIGN PATENT DOCUMENTS

| | | | |
|---|---|---|---|
| JP | 57-173054 | | 10/1982 |
| JP | 60116350 | A | 6/1985 |
| JP | 60168452 | | 8/1985 |
| JP | 60168452 | A | 8/1985 |
| JP | 584263 | A | 4/1993 |
| JP | 5084263 | | 4/1993 |
| JP | 05084263 | A | 4/1993 |

OTHER PUBLICATIONS

European Office Action and Search Report issued in corresponding EP Application No. 09816092.2, dated Feb. 1, 2013.
Chinese Office Action issued in corresponding CN Application No. 2009-80144795.0, dated Feb. 4, 2013.
International Search Report for PCT/JP2009/066228 mailed Dec. 15, 2009.
Office Action dated Jan. 3, 2014, corresponds to European patent application No. 09816092.2.
Office Action dated Sep. 6, 2013, corresponds to Chinese patent application No. 200980144795.0.
Office Action issued Oct. 1, 2014, corresponding to Australian patent application No. 2009297657.

* cited by examiner

TIP END ←——→ REAR END

TIP END ←——→ REAR END

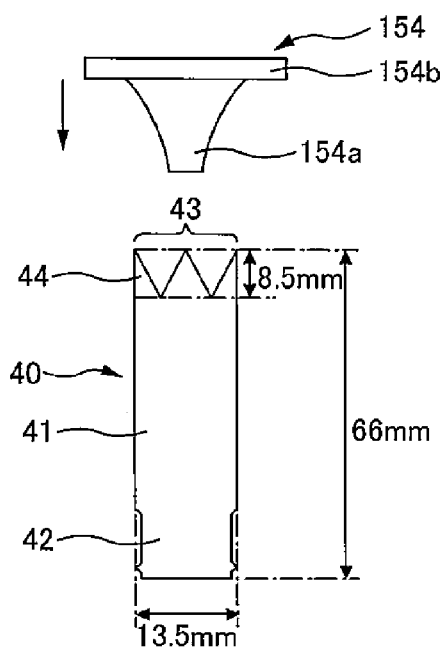
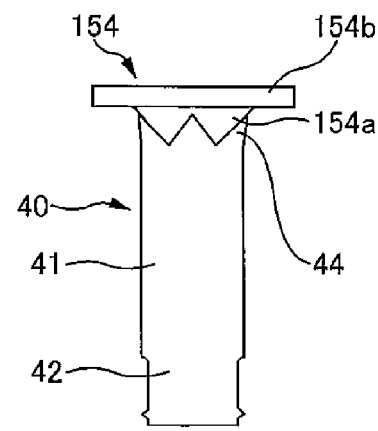
FIG. 10A    FIG. 10B
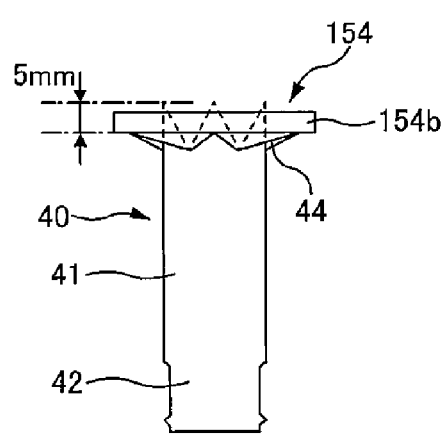
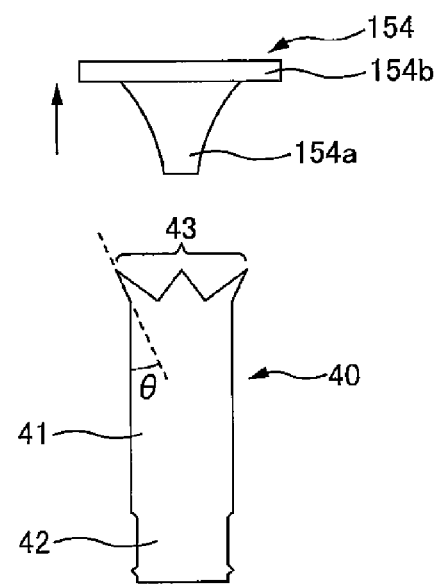
FIG. 10C    FIG. 10D

MANUFACTURING APPARATUS AND MANUFACTURING METHOD OF TAMPON

RELATED APPLICATIONS

The present application is a national phase of PCT/JP2009/066228, filed Sep. 19, 2009 and is based on, and claims priority from, Japanese Application Number 2008-251448, filed Sep. 29, 2008.

TECHNICAL FIELD

The present invention relates to an apparatus and a method for manufacturing a tampon. Particularly, the present invention relates to an apparatus and a method for manufacturing a tampon including a tampon main body with a cord, an accommodating cylinder that accommodates the tampon main body, and a pushing member that moves inside the accommodating cylinder and pushes the tampon main body out of the accommodating cylinder, in which a plurality of petaloid parts are provided in a leading end part of the accommodating cylinder by surrounding a leading-end opening of the accommodating cylinder.

BACKGROUND ART

A tampon is known as a sanitary product. Of the tampons, there is a tampon including a tampon main body with a cord, an accommodating cylinder that accommodates the tampon main body, and a pushing member that moves inside the accommodating cylinder and pushes the tampon main body out of the accommodating cylinder, in which a plurality of petaloid parts are provided in a leading end part of the accommodating cylinder by surrounding a leading-end opening of the accommodating cylinder. Such tampon is manufactured by manufacturing each item which constitutes the tampon, that are, the tampon main body, the accommodating cylinder, and the pushing member, and inserting each of the pushing member and the tampon main body into the accommodating cylinder through the leading-end opening of the accommodating cylinder.

By the way, the tampon main body is inserted into the accommodating cylinder from the side including the cord. Also, there is a case of using a guide tube as an inserting jig in the case of inserting the tampon main body (refer to PTL 1 for example). This guide tube is for guiding the tampon main body so as to smoothly insert the tampon main body into the accommodating cylinder. In detail, the tampon main body is inserted into the guide tube and pressed. Thereby the tampon main body inside the guide tube moves along the guide tube, and in the case where the leading-end opening of the accommodating cylinder is disposed at the leading end of the guide tube (that is, destination of the tampon main body), the tampon main body can be inserted into the accommodating cylinder from the guide tube.

CITATION LIST

Patent Literature

PTL 1: JP-A-60-116350

SUMMARY OF INVENTION

Problems to be Solved by the Invention

However, in a case of inserting the tampon main body inserted into the guide tube into the accommodating cylinder, in a state where the guide tube and the accommodating cylinder are separated each other and the petaloid part of the accommodating cylinder is exposed, the cord included in the tampon main body may get caught by the petaloid part. That is, in a state where the cord easily contacts the petaloid part at the time of inserting the tampon main body into the accommodating cylinder, it is difficult to properly insert the tampon main body into the accommodating cylinder.

The present invention was made in view of the foregoing conventional problem, and it is an advantage thereof to properly insert the tampon main body into the accommodating cylinder.

Means for Solving the Problems

A main aspect of the invention for achieving the foregoing object is an apparatus for manufacturing a tampon, the tampon including a tampon main body having a cord, an accommodating cylinder accommodating the tampon main body, a pushing member moving inside the accommodating cylinder and pushing the tampon main body out of the accommodating cylinder, a plurality of petaloid parts provided in a leading-end part of the accommodating cylinder by surrounding a leading-end opening of the accommodating cylinder, including:

a pushing-member inserting mechanism that inserts the pushing member into the accommodating cylinder through the leading-end opening; and a tampon main body inserting mechanism that inserts the tampon main body into the accommodating cylinder from side including the cord through the leading-end opening, the tampon main body inserting mechanism including:

a guide tube guiding the tampon main body inserted into the guide tube;

a drive section connecting the guide tube and the accommodating cylinder by moving one of the guide tube and the accommodating cylinder towards the other and thus contacting the guide tube and the leading-end part of the accommodating cylinder;

a pressing part pressing the tampon main body inserted into the guide tube so as to insert the tampon main body into the accommodating cylinder connected to the guide tube; and an air suction device sucking air from rear-end side of the accommodating cylinder in a case where the tampon main body is inserted into the accommodating cylinder.

Other features of the invention will become clear by the description of the present specification and the accompanying drawings.

Effect of the Invention

According to the invention, a tampon main body can be properly inserted into an accommodating cylinder.

BRIEF DESCRIPTION OF DRAWINGS

FIGS. 10A to 10D are explanatory diagrams of a bending process.

DESCRIPTION OF EMBODIMENTS

Figure 1:
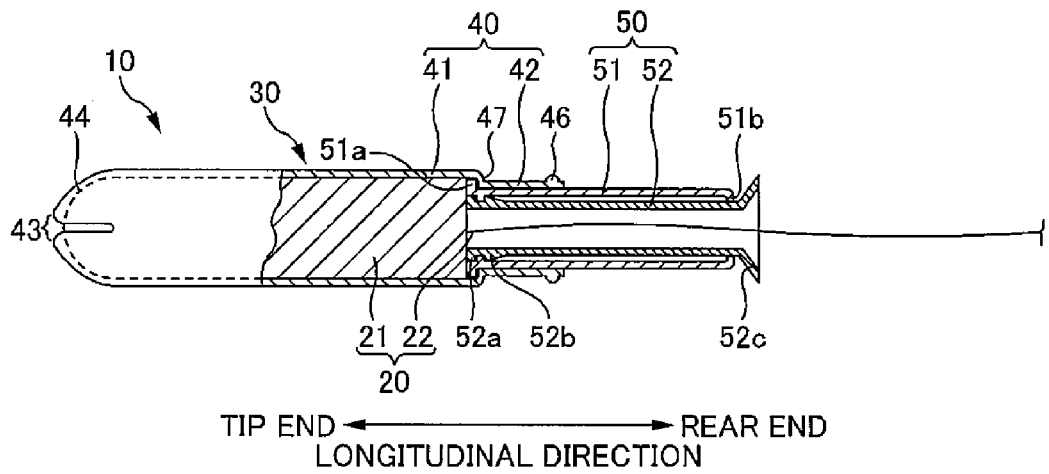
FIG. 1 is a cross-sectional view showing components of a tampon 10 (first view).

At least the following matters will be made clear by the description in the present specification and the accompanying drawings.

First, an apparatus for manufacturing a tampon, the tampon including a tampon main body having a cord, an accommodating cylinder accommodating the tampon main body, a pushing member moving inside the accommodating cylinder and pushing the tampon main body out of the accommodating cylinder, a plurality of petaloid parts provided in a leading-end part of the accommodating cylinder by surrounding a leading-end opening of the accommodating cylinder, including:

a pushing-member inserting mechanism that inserts the pushing member into the accommodating cylinder through the leading-end opening; and a tampon main body inserting mechanism that inserts the tampon main body into the accommodating cylinder from side including the cord through the leading-end opening, the tampon main body inserting mechanism including:

a guide tube guiding the tampon main body inserted into the guide tube;

a drive section connecting the guide tube and the accommodating cylinder by moving one of the guide tube and the accommodating cylinder towards other one and thus contacting the guide tube and the leading-end part of the accommodating cylinder;

a pressing part pressing the tampon main body inserted into the guide tube so as to insert the tampon main body into the accommodating cylinder connected to the guide tube; and an air suction device sucking air from rear-end side of the accommodating cylinder in a case where the tampon main body is inserted into the accommodating cylinder.

According to such an apparatus for manufacturing a tampon, in a case of inserting the tampon main body inserted into the guide tube into the accommodating cylinder, the cord provided to the tampon main body is prevented from contacting the petaloid part of the accommodating cylinder. As a result, the cord is prevented from being caught into the petaloid part and thus the tampon main body can be properly inserted into the accommodating cylinder.

In the apparatus for manufacturing a tampon, it is preferable that the guide tube includes an airhole formed at an outer peripheral part of the guide tube. With such a structure, in the case of inserting the tampon main body inserted into the guide tube into the accommodating cylinder, the air suction device sucks air so that the cord of the tampon main body extends straightly towards the leading-end opening of the accommodating cylinder. Thereby, the tampon main body can be properly inserted into the accommodating cylinder from the side including the cord.

In the apparatus for manufacturing a tampon, it is preferable that the apparatus for manufacturing a tampon includes other tampon main body inserting mechanism inserting the tampon main body into the guide tube, wherein the drive section connects the guide tube and the accommodating cylinder by moving the guide tube in a state of holding the tampon main body inserted by the other tampon main body inserting mechanism towards the accommodating cylinder and thus contacting the guide tube and the leading-end part of the accommodating cylinder, and length of the guide tube in the longitudinal direction is longer than length from leading end to rear end of the tampon main body in a state where the cord is extended. With such a structure, the guide tube and the accommodating cylinder can be connected in a state where the cord of the tampon main body is accommodated in the guide tube. Thereby, the cord can be prevented from being caught into the petaloid part in a case where the guide tube and the accommodating cylinder are connected.

In the apparatus for manufacturing a tampon, it is preferable that the guide tube is held in a state where the longitudinal direction of the guide tube is lying along vertical direction, the other tampon main body inserting mechanism inserts the tampon main body from opposite side of side including the cord into the guide tube from downside of the guide tube. With such a structure, the cord of the tampon main body does not hamper inserting the tampon main body into the guide tube. Thus, the tampon main body can be smoothly inserted into the guide tube.

In the apparatus for manufacturing a tampon, it is preferable that the apparatus for manufacturing a tampon includes a bending mechanism performing a bending process, a process of bending each of the plurality of petaloid parts outwardly in the radial direction of the accommodating cylinder, to the accommodating cylinder, the guide tube including:

a tapered part provided in one end part in the longitudinal direction of the guide tube wherein an internal diameter of the tapered part becomes smaller from one end of the guide tube toward other end; and a cylindrical part adjacent to the tapered part at other end side of the tapered part in the longitudinal direction of the guide tube, wherein the drive section moves the guide tube toward the accommodating cylinder on which the bending process is performed, and inserts the accommodating cylinder into the guide tube from one end side in the longitudinal direction of the guide tube, the guide tube guides the leading-end part of the accommodating cylinder into the cylindrical part by contacting a leading end of the petaloid part at an inner peripheral surface of the tapered part, in a case of inserting the accommodating cylinder into the guide tube, and by fitting the leading-end part into the cylindrical part and contacting the petaloid part, the guide tube is connected to the accommodating cylinder. With such a structure, the guide tube and the accommodating cylinder can be smoothly connected.

In the apparatus for manufacturing a tampon, it is preferable that the cylindrical part includes a first cylindrical part and a second cylindrical part provided in a position between the first cylindrical part and the tapered part in the longitudinal direction of the guide tube, the pressing part presses the tampon main body so that the tampon main body moves inside the first cylindrical part, by fitting the leading-end part of the accommodating cylinder into the second cylindrical part, the guide tube is connected to the accommodating cylinder by contacting the petaloid part at an inner peripheral surface of the second cylindrical part, and in a case where the leading-end part is fitted into the second cylindrical part, an inner peripheral surface of the first cylindrical part is positioned inward than the petaloid part contacting the inner peripheral surface of the second cylindrical part in the radial direction of the guide tube. With such a structure, it is possible to regulate the cord of the tampon main body touching the petaloid part at the time of the tampon main body moving inside the guide tube. Thus, the tampon main body inserted into the guide tube can be properly inserted into the outer cylinder 40 without the cord being caught by the petaloid part.

In the apparatus for manufacturing a tampon, it is preferable that the apparatus for manufacturing a tampon includes a bending mechanism performing a bending process, a process of bending each of the plurality of petaloid parts outwardly in the radial direction of the accommodating cylinder, to the accommodating cylinder, wherein the drive section moves the guide tube towards the accommodating cylinder on which the bending process is performed and inserts one end part in the longitudinal direction of the guide tube from the leading-end opening into the accommodating cylinder, and thus contacts the one end part in the longitudinal direction of the guide tube with the leading-end part of the accommodating cylinder and connects the guide tube and the accommodating cylinder. With such a structure, the guide tube and the accommodating cylinder can be smoothly connected.

Further, it is possible to realize a method of manufacturing a tampon, the tampon including a tampon main body having a cord, an accommodating cylinder accommodating the tampon main body, a pushing member moving inside the accommodating cylinder and pushing the tampon main body out of the accommodating cylinder, a plurality of petaloid parts provided in a leading-end part of the accommodating cylinder by surrounding a leading-end opening of the accommodating cylinder, including:

inserting the pushing member into the accommodating cylinder through the leading-end opening; and inserting the tampon main body into the accommodating cylinder from side including the cord through the leading-end opening, inserting the tampon main body into the accommodating cylinder including:

connecting a guide tube and the accommodating cylinder by moving one of the guide tube guiding the tampon main body inserted into the guide tube and the accommodating cylinder towards other one and contacting the guide tube and the leading-end part of the accommodating cylinder;

pressing the tampon main body inserted into the guide tube so as to insert the tampon main body into the accommodating cylinder connected to the guide tube; and sucking air from rear-end side of the accommodating cylinder in a case where the tampon main body is inserted into the accommodating cylinder. With such a manufacturing method, the tampon main body can be properly inserted into the accommodating cylinder.

===Structure of Tampon===

At describing an apparatus and a method for manufacturing a tampon of the present invention, the structure of a tampon 10 manufactured by such apparatus and method of manufacturing will be described with reference to FIGS. 1 through 6.

Figure 2:
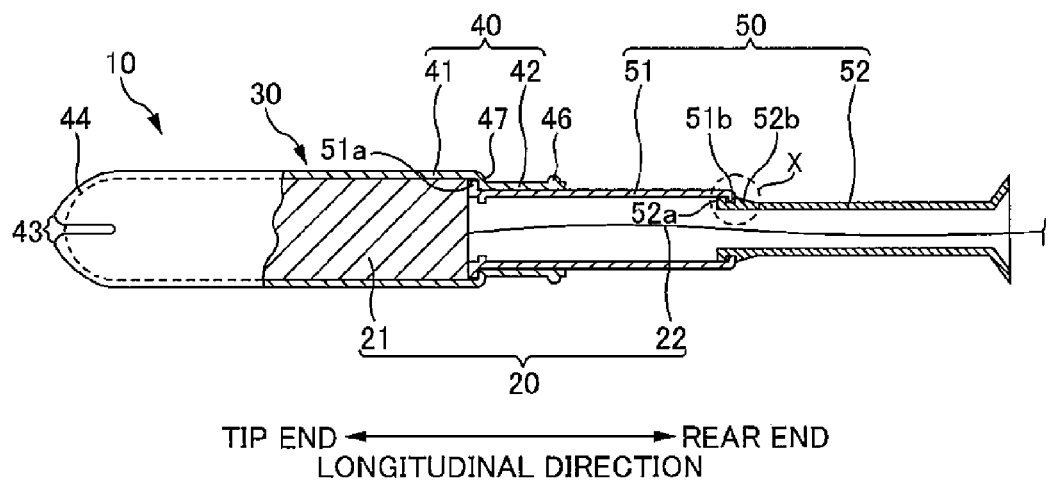
FIG. 2 is a cross-sectional view showing components of a tampon 10 (second view).
Figure 3:
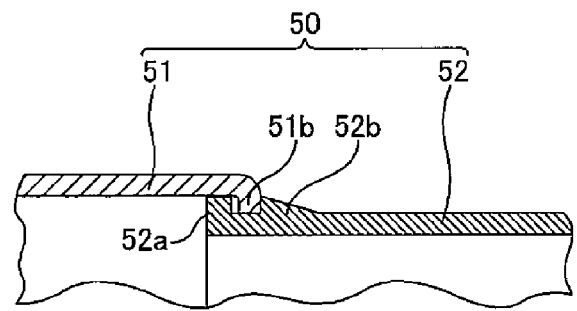
FIG. 3 is a diagram showing how a first inner cylinder 51 and a second inner cylinder 52 are connected.
Figure 4A:
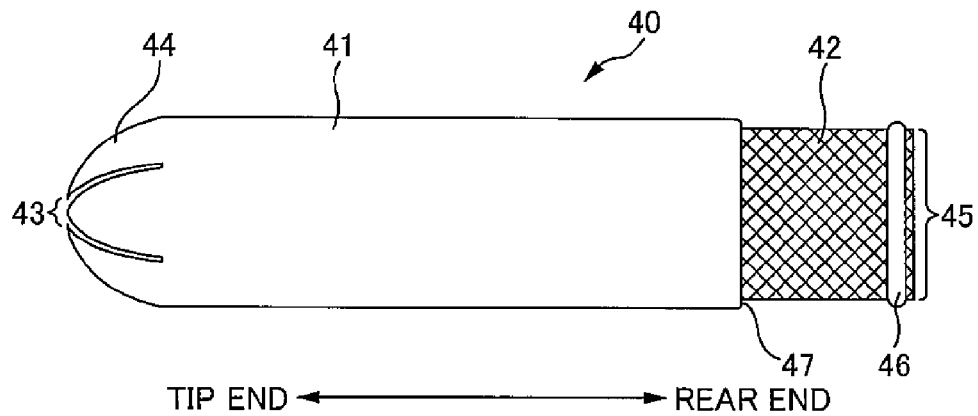
FIGS. 4A and 4B are external views of an outer cylinder 40.
Figure 4B:
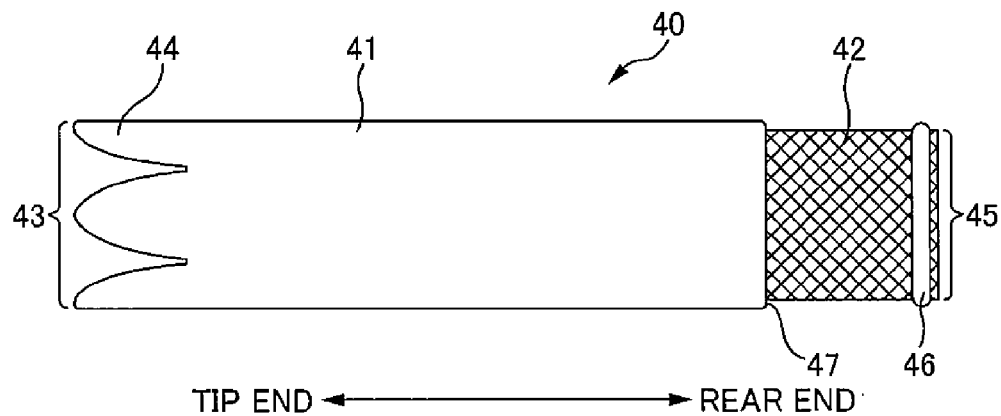
Figure 4C:
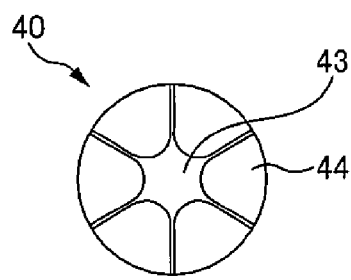
FIG. 4C is a diagram seeing the outer cylinder 40 shown in FIG. 4A from its leading-end side.
Figure 5:
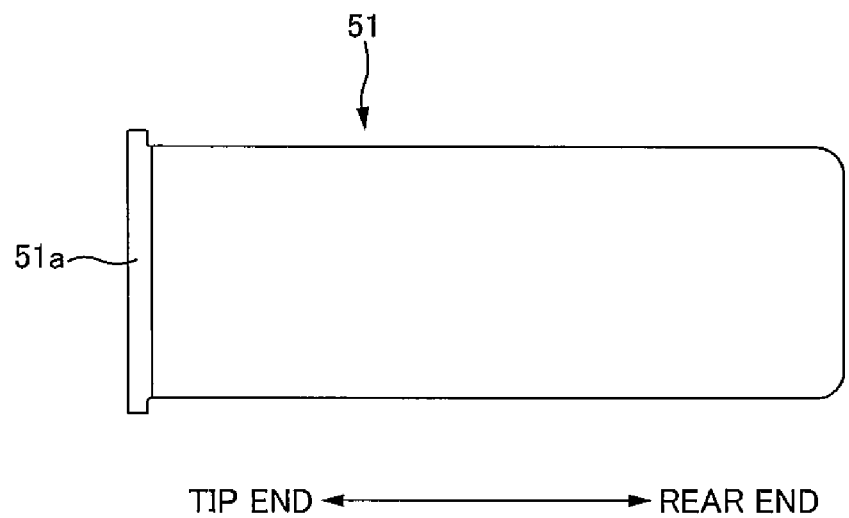
FIG. 5 is an external view of the first inner cylinder 51.
Figure 6:
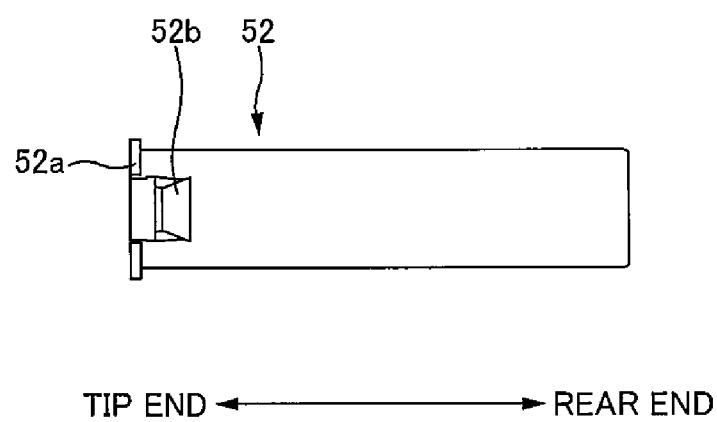
FIG. 6 is an external view of the second inner cylinder 52.

FIGS. 1 and 2 are cross-sectional views showing components of the tampon 10. FIG. 1 shows the tampon 10 in a state of an inner cylinder 50 being contracted, and FIG. 2 shows the tampon 10 in a state of the inner cylinder 50 being extended. FIG. 3 is a diagram showing how a first inner cylinder 51 and a second inner cylinder 52 are connected, and is an enlarged view of an area represented by symbol "X" in FIG. 2. FIGS. 4A and 4B are external views of an outer cylinder 40. FIG. 4C is a diagram of the outer cylinder 40 described in FIG. 4A viewed from its leading-end side. FIG. 5 is an external view of the first inner cylinder 51. FIG. 6 is an external view of the second inner cylinder 52. In the description hereafter, of the longitudinal direction of the tampon 10, a side that is inserted into a vaginal cavity is referred to as a leading-end side, and an opposite side thereof is referred to as a rear-end side.

As shown in FIG. 1, the tampon 10 of the embodiment is a sanitary product including a tampon main body 20 and an applicator 30. As shown in the diagram, the tampon main body 20 includes a cotton body 21 and a cord 22 that is sewn on the cotton body 21. The cotton body 21 is an absorbent body that blocks the vaginal cavity and absorbs menstrual blood and the like. The cotton body 21 is formed by cutting a cotton strip covered with nonwoven fabric on both sides and by shaping into a substantially bullet like shape by heat forming after pressing the cotton strip. In the present embodiment, the diameter of the cotton body 21 is within the range from 11 mm to 12 mm. The cord 22 extends from the rear-end side of the cotton body 21 and is held by a user at the time of pulling out the cotton body 21 inside the vaginal cavity. As shown in FIG. 1, the cord 22 is extended through the applicator 30 and somewhat extended out from rear end of the applicator 30.

The applicator 30 is an aid for smoothly guiding the tampon main body 20 (specifically the cotton body 21) into the vaginal cavity. As shown in FIG. 1, the applicator 30 includes the outer cylinder 40 as an example of accommodating cylinder for accommodating the tampon main body 20, and the inner cylinder 50 as an example of pushing member for pushing out the tampon main body 20 accommodated in the outer cylinder 40.

The outer cylinder 40 is a cylindrical body with an appropriate flexibility formed by injection molding a thermoplastic resin. The outer cylinder 40 includes a major diameter part 41 provided on a leading-end part, and a minor diameter part 42 provided on a rear-end part that has a smaller external diameter than the major diameter part 41. The major diameter part 41 is a part having an internal diameter that is slightly longer than the diameter of the tampon main body 20, and accommodates the tampon main body 20 therein. And at the time of using the tampon 10, the major diameter part 41 is inserted into the vaginal cavity while accommodating the tampon main body 20 therein. The tampon main body 20 is accommodated in the major diameter part 41 so as to contact its outer peripheral surface with an inner peripheral surface of the major diameter part 41. The minor diameter part 42 is a part held by a user at the time of using the tampon 10. However, the minor diameter part 42 does not have to be included in the outer cylinder 40.

As shown in FIGS. 4A and 4B, the outer cylinder 40 includes a leading-end opening 43 and a plurality of petaloid parts 44 (in this embodiment, six petaloid parts) surrounding the leading-end opening 43. Each of the plurality of petaloid parts 44 is formed at the leading-end part of the outer cylinder 40, and is inwardly bent in an arc in radial direction of the outer cylinder 40 at the time of shipping the tampon 10 as shown in FIG. 4A. Therefore, at the time of inserting the outer cylinder 40 into the vaginal cavity, the leading-end part of the outer cylinder 40 is in a substantially hemispherical shape as shown in FIGS. 1 and 2, and the leading-end opening 43 is in substantially closed state as shown in FIG. 4C. On the other hand, as shown in FIG. 4B, in the outer cylinder 40 just after being injection molded, each of the plurality of petaloid parts 44 is opened, and thus the leading-end opening 43 is in an opened state.

Further, as shown in FIG. 4A, the outer cylinder 40 includes a rear-end opening 45, and an annular rib 46 provided at a position slightly the leading-end side than the rear-end opening 45. Further, an annular stepped part 47 is formed between the major diameter part 41 and the minor diameter part 42.

The inner cylinder 50 is a cylindrical body inserted into the minor diameter part 42 of the outer cylinder 40. The inner cylinder 50 is positioned in the rear-end side of the tampon main body 20 in the outer cylinder 40, and moves along central axis direction of the outer cylinder 40 to push forward the tampon main body 20 from back towards the leading-end opening 43. Thereby, the tampon main body 20 is pushed out of the outer cylinder 40 by pushing each of the plurality of petaloid parts 44 outwardly in the radial direction of the outer cylinder 40 (in other words, by opening the leading-end opening 43). That is to say, the inner cylinder 50 can move inside the outer cylinder 40 and has a function of pushing out the tampon main body 20 out of the outer cylinder 40 through the leading-end opening 43.

It is to be noted that the inner cylinder 50 of the present embodiment has an extendable structure for making overall length of the tampon 10 compact. In detail, when the inner cylinder 50 contracts as shown in FIG. 1, the length of the inner cylinder 50 becomes shorter than the outer cylinder 40 and becomes a length suitable for carrying the tampon 10. On the other hand, when the inner cylinder 50 expands as shown in FIG. 2, the length of the inner cylinder 50 becomes a length sufficient for pushing the tampon main body 20 out of the outer cylinder 40. As described above, in order to make the inner cylinder 50 extendable, in this embodiment, the inner cylinder 50 is two-tier structure. In detail, as shown in FIG. 1, the inner cylinder 50 of the present embodiment includes the first inner cylinder 51 and the second inner cylinder 52 slidably inserted into the first inner cylinder 51.

The first inner cylinder 51 is a cylindrical body formed by injection molding plastics. The first inner cylinder 51 has an external diameter that is slightly smaller than an internal diameter of the minor diameter part 42 of the outer cylinder 40. As shown in FIG. 1, the first inner cylinder 51 is slidably inserted into the minor diameter part 42. As shown in FIG. 5, an annular flange part 51a is formed on an outer peripheral surface of the leading-end part of the first inner cylinder 51.

The flange part 51a has an external diameter that is slightly smaller than the major diameter part 41 of the outer cylinder 40, and is engaged with an inner wall face of the stepped part 47 so as to prevent the inner cylinder 50 falling through the rear-end opening 45 of the outer cylinder 40. At the time of the inner cylinder 50 pushing the tampon main body 20 out of the outer cylinder 40, the inner cylinder 50 moves so that an outer peripheral surface of the flange part 51a contacts an inner peripheral surface of the major diameter part 41. Further, as shown in FIGS. 1 and 2, at a rear-end part of an inner peripheral surface of the first inner cylinder 51 an annular protrusion 51b is provided by protruding inwardly in the radial direction of the first inner cylinder 51.

The second inner cylinder 52 is a cylindrical body formed by injection molding a thermoplastic resin. The second inner cylinder 52 has an external diameter that is slightly smaller than an internal diameter of the first inner cylinder 51. In a case where the inner cylinder 50 is in a contracted state the second inner cylinder 52 is inserted into the first inner cylinder 51 as shown in FIG. 1. And in a case where the inner cylinder 50 is in an expanded state the second inner cylinder 52 is connected to a rear-end part of the first inner cylinder 51 at a leading-end part thereof as shown in FIG. 2. Further, as shown in FIG. 6, on an outer peripheral surface of the leading-end part of the second inner cylinder 52, an arcuate flange part 52a and a protruded part 52b positioned in the rear-end side of the flange part 52a are formed. As shown in FIG. 3, the height of the protruded part 52b becomes lower as it goes to the rear end. And the gap between the flange part 52a and the protruded part 52b of the second inner cylinder 52 is slightly thicker than the thickness of the annular protrusion 51b of the first inner cylinder 51.

In the case where the second inner cylinder 52 is pulled to the rear-end side, the annular protrusion 51b of the first inner cylinder 51 is located between the flange part 52a of the second inner cylinder 52 and the protruded part 52b. In such a state, as shown in FIG. 3, the annular protrusion 51b is engaged with the flange part 52a and the protruded part 52b and thus the first inner cylinder 51 and the second inner cylinder 52 are connected.

Further, as shown in FIGS. 1 and 2, a flared part 52c is formed at a rear-end part of the second inner cylinder 52. Preferably, an external diameter of the flared part 52c is at least greater than the internal diameter of the first inner cylinder 51, and greater than or equal to the internal diameter of the minor diameter part 42 of the outer cylinder 40.

===Outline of Method of Manufacturing Tampon 10===

Figure 7A:
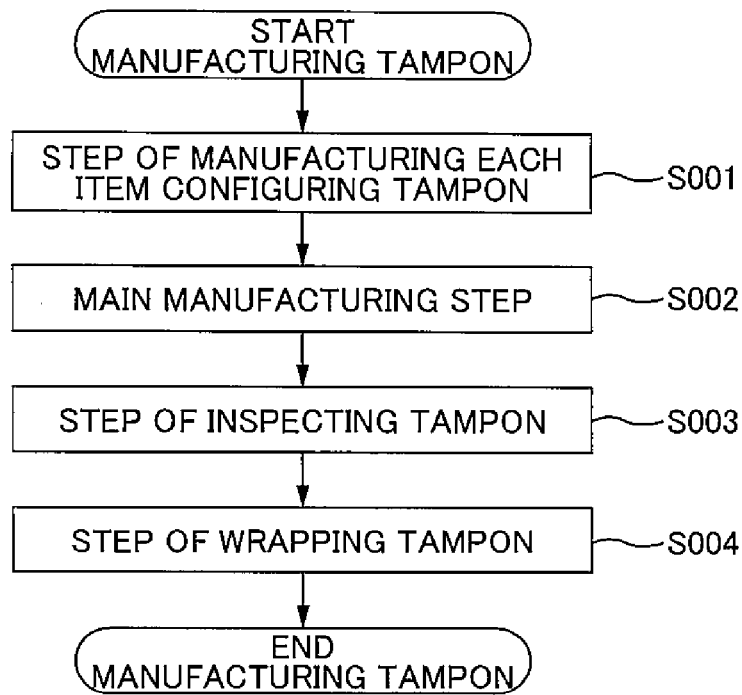
FIGS. 7A and 7B are flowcharts showing the manufacturing of the tampon 10.
Figure 7B:
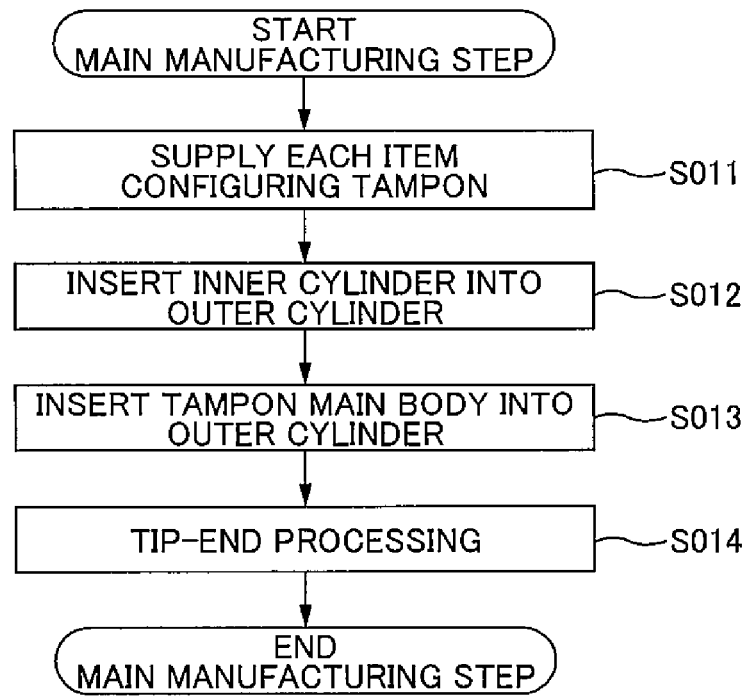

Next, a method of manufacturing the tampon 10 of the present embodiment will be described with reference to FIGS. 7A to 8D. FIGS. 7A to 7B are flowcharts showing how the tampon 10 is manufactured. FIGS. 8A to 8D are diagrams in a series showing how the tampon 10 is manufactured.

As shown in FIG. 7A, the method of manufacturing the tampon 10 includes a step of manufacturing each item constituting the tampon 10 (S001), a step of supplying the manufactured items to an assembly apparatus 100 described later, and assembling and thus manufacturing the tampon 10 (hereafter, a main manufacturing step S002), a step of inspecting the manufactured tampon 10 (S003), and a step of wrapping the tampon 10 (S004).

Figure 8A:
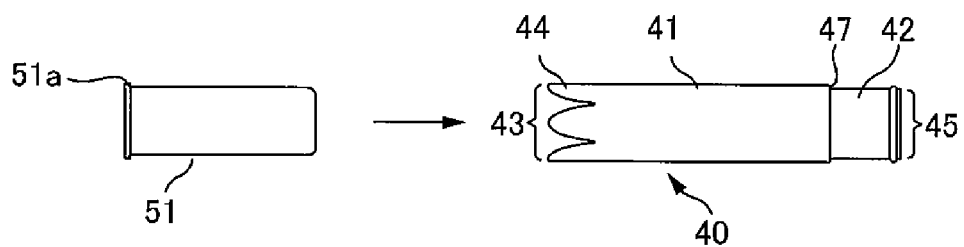
FIGS. 8A to 8D are diagrams in a series showing how the tampon 10 is manufactured.

In the main manufacturing step S002, firstly, each of the items constituting the tampon 10 is supplied to the assembling apparatus 100 as shown in FIG. 7B (S011). As shown in FIG. 8A, at the time of being supplied to the assembling apparatus 100, the outer cylinder 40 is in a state where each of the plurality of petaloid parts 44 is in an opened state (in other words, in a state where the leading-end opening 43 is opened).

Next, a process of inserting the inner cylinder 50 into the outer cylinder 40 through the leading-end opening 43 is performed (S012). This process is performed by an inner cylinder inserting mechanism 130 to be described later. In present embodiment, the inner cylinder 50 consists of the first inner cylinder 51 and the second inner cylinder 52 as described before. Thus, in the embodiment, the first inner cylinder 51 is inserted into the outer cylinder 40 in the first place, and the second inner cylinder 52 is inserted into the outer cylinder 40 subsequently.

Next, process of inserting the tampon main body 20 into the outer cylinder 40 through the leading-end opening 43 is performed (S013). This process is performed by a tampon main body inserting mechanism 140 to be described later. When the tampon main body 20 is inserted into the outer cylinder 40, the assembly of the tampon 10 is complete. Now, the procedure of inserting the tampon main body 20 and the inner cylinder 50 into the outer cylinder 40 is described in detail.

Figure 8B:
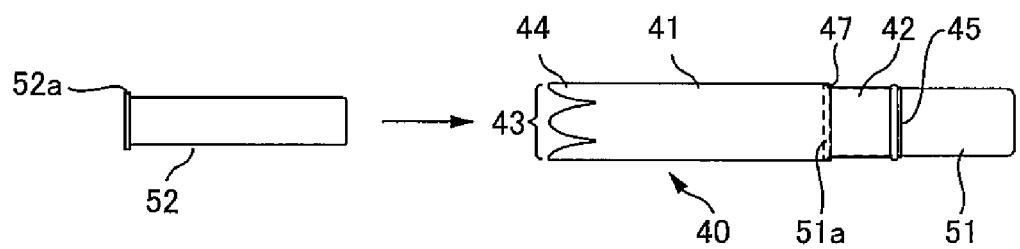

First, as shown in FIG. 8A, the first inner cylinder 51 is inserted into the outer cylinder 40 through the leading-end opening 43 of the outer cylinder 40. The first inner cylinder 51 inserted into the outer cylinder 40 will be in a state where its rear-end part protrudes through the rear-end opening 45 of the outer cylinder 40 and the flange part 51a is engaged with the inner wall face of the stepped part 47 of the outer cylinder 40 (see FIG. 8B). Then, as shown in FIG. 8B, the second inner cylinder 52 is inserted into the outer cylinder 40 through the leading-end opening 43. The second inner cylinder 52 inserted into the outer cylinder 40 will be in a state where its rear-end part protrudes through the opening on the rear-end side of the first inner cylinder 51 and the flange part 52a is engaged with the inner peripheral surface of the first inner cylinder 51 (see FIG. 8C). It is to be noted that, as shown in FIG. 8B, a flared part 52c is not yet formed on the second inner cylinder 52 at the time in which the second inner cylinder 52 is being supplied to the assembling apparatus 100. After the second inner cylinder 52 has been inserted into the outer cylinder 40, the flared part 52c is formed by heat forming the rear-end part of the second inner cylinder 52. By following the above-described processes, the assembly of the applicator 30 is complete.

Figure 8C:
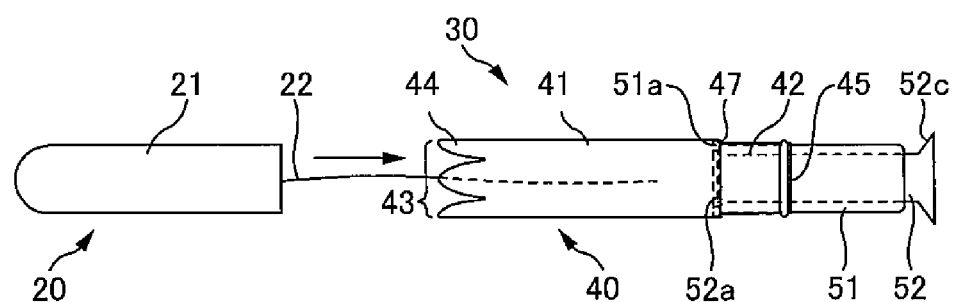

Then, as shown in FIG. 8C, the tampon main body 20 is inserted into the outer cylinder 40 through the leading-end opening 43. Here, as shown in FIG. 8C, the tampon main body 20 is inserted from side including the cord 22. Thus, the tampon main body 20 is accommodated in the outer cylinder 40 by facing correct direction. When the tampon main body 20 is inserted into the outer cylinder 40, the cotton body 21 is accommodated in the major diameter part 41 of the outer cylinder 40 and the cord 22 extends out from the rear end of the applicator 30 (specifically, out of the opening on the rear-end side of the second inner cylinder 52).

Figure 8D:
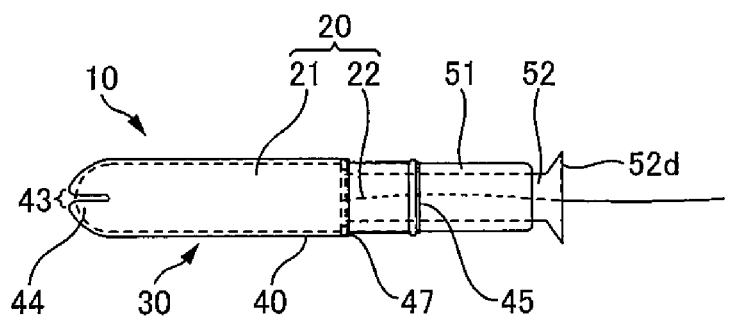

After assembling of the tampon 10 is finished, as shown in FIG. 8D, a process of heat forming is performed in which the leading-end part of the outer cylinder 40 is formed into a substantially hemispherical shape by bending each of the plurality of petaloid parts 44 in such a manner that it is inclined inwardly in the radial direction of the outer cylinder 40 (hereinafter, referred to as a leading-end processing) (S014). When the leading-end processing is terminated, the tampon 10 is complete and the main manufacturing step S002 is complete.

It is to be noted that, as described below, the assembling apparatus 100 includes a transport conveyor 110 (see FIG. 9). This transport conveyor 110 intermittently carries out movement of transporting the assembled products in transport direction (transportation movement). Between the transportation movement, (that is, while the assembled item is in a rest) each of the above-mentioned processes is sequentially performed on the transport conveyor 110.

==Assembling Apparatus 100 of Tampon 10==

Figure 9:
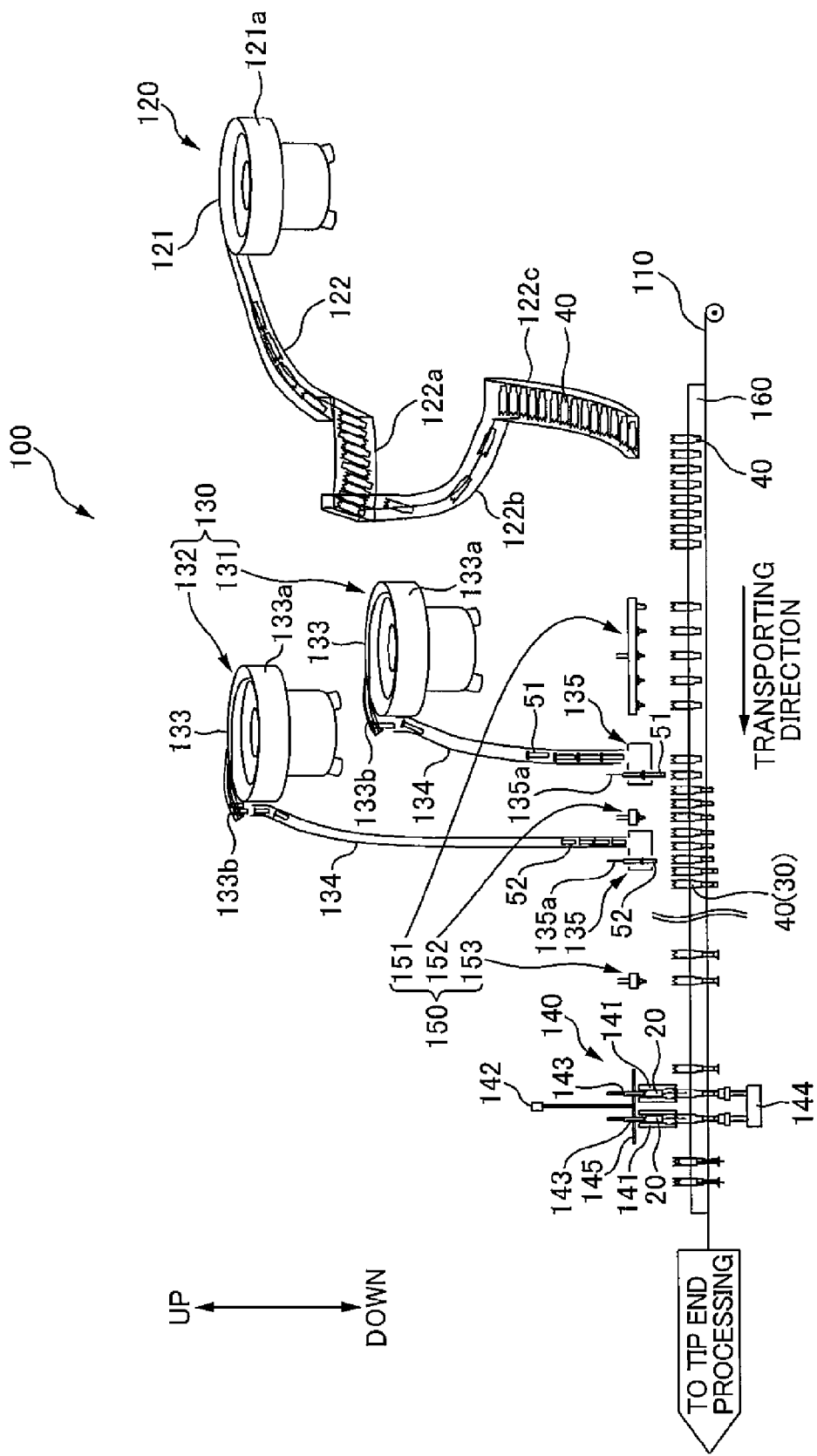
FIG. 9 is a schematic view of an assembling apparatus 100.

Of the main manufacturing step S002 described above, a series of the processes of assembling the tampon 10 is performed by the assembling apparatus 100 shown in FIG. 9. FIG. 9 is a schematic diagram showing the assembling apparatus 100. This assembling apparatus 100 is an example of an apparatus for manufacturing the tampon 10. As shown in FIG. 9, the assembling apparatus 100 includes the transport conveyor 110, an outer cylinder supplying mechanism 120, an inner cylinder inserting mechanism 130 as an example of pushing-member inserting mechanism, a tampon main body inserting mechanism 140 and a bending mechanism 150. Hereinafter, each device that constitutes the assembling apparatus 100 will be described.

(1) Transport Conveyor 110

The transport conveyor 110 is a device that transports the outer cylinder 40 and items inserted into the outer cylinder 40 (first inner cylinder 51, second inner cylinder 52 and tampon main body 20) in the transport direction (direction shown by an arrow in FIG. 9). Amount 160 that mounts the outer cylinder 40 thereon is placed on the transport conveyor 110 and the mount 160 is transported in the transport direction by the transport conveyor 110. Thereby, the outer cylinder 40 mounted on the mount 160 and the items inserted in the outer cylinder 40 are transported in the transport direction together with the mount 160. Circular holes (not shown) are formed on the mount 160 along vertical direction. The outer cylinder 40 is mounted on the mount 160 by being fitted into the circular hole from side of the minor diameter part 42.

As shown in FIG. 9, the outer cylinder 40 is mounted on the mount 160 in a state where the central axis direction of the outer cylinder 40 parallels the vertical direction and the leading-end opening 43 is facing substantially upwards (that is, in a state of being stand-up). In this embodiment, as shown in FIG. 9, in a state where the outer cylinder 40 is mounted on the mount 160, substantially half of the leading-end side of the outer cylinder 40 is exposed. Therefore, in the state where the outer cylinder 40 is mounted on the mount 160, each of the plurality of petaloid parts 44 is exposed from leading end of the petaloid part 44 to rear end of the petaloid part 44.

(2) Outer Cylinder Supplying Mechanism 120

The outer cylinder supplying mechanism 120 is a mechanism that supplies the injection molded outer cylinder 40 to the transport conveyor 110. As shown in FIG. 9, the outer cylinder supplying mechanism 120 includes an outer cylinder feeder 121, a supplying path 122 connected to a vibratory table 121a included in the outer cylinder feeder 121, and an outer cylinder setting part (not shown) that sets the outer cylinder 40 that has passed through the supplying path 122 to the mount 160.

The outer cylinder feeder 121 is a parts feeder having the bowl-shaped vibratory table 121a and transports the outer cylinder 40 placed on the vibratory table 121a by vibrating the vibratory table 121a. The outer cylinder 40 that has moved on the vibratory table 121a is passed to the supplying path 122.

As shown in FIG. 9, accumulating parts 122a and 122c that temporarily accumulate the outer cylinders 40 are provided at middle part and end part of the supplying path 122. The plurality of outer cylinders 40 are accumulated in each of the accumulating parts 122a and 122c in a state of lying down. A drop chute 122b is formed between the accumulating parts 122a and 122c. The outer cylinders 40 accumulated in the accumulating part 122a provided at the middle part of the supplying path 122 sequentially drop into the drop chute 122b. It is to be noted that in the drop chute 122b, a restriction mechanism (not shown) for restricting the orientation of the outer cylinder 40 into a predetermined orientation is provided. While passing through the drop chute 122b, the outer cylinder 40 is subjected to the action of the restriction mechanism and thus its orientation is restricted in such a manner that the rear-end part of the outer cylinder 40 comes out from the drop chute 122b first.

Then, the outer cylinder setting part sequentially catches the outer cylinders 40 that slid down the drop chute 122b and thus accumulated in the accumulating part 122c, and mounts the received outer cylinder 40 onto the mount 160 placed on the transport conveyor 110.

(3) Inner Cylinder Inserting Mechanism 130

The inner cylinder inserting mechanism 130 inserts the inner cylinder 50 into the outer cylinder 40 through the leading-end opening 43 of the outer cylinder 40. Further, the inner cylinder inserting mechanism 130 each includes a mechanism that inserts the first inner cylinder 51 into the outer cylinder 40 (hereinafter referred to as a first inner cylinder inserting mechanism 131) and a mechanism that inserts the second inner cylinder 52 into the outer cylinder 40 (hereinafter referred to as a second inner cylinder inserting mechanism 132).

As shown in FIG. 9, the first inner cylinder inserting mechanism 131 includes an inner cylinder feeder 133, an inner cylinder pressing part 135 that inserts the first inner cylinder 51 into the outer cylinder 40 by pressing it, and a tube 134 provided between the inner cylinder feeder 133 and the inner cylinder pressing part 135.

The inner cylinder feeder 133 is a parts feeder having a bowl-shaped vibratory table 133a and moves the first inner cylinders 51 placed on the vibratory table 133a. As shown in FIG. 9, a terminal end part of the vibratory table 133a is connected to a pair of rails 133b. Between the pair of rails 133b, a gap that is slightly larger than the external diameter of the first inner cylinder 51 is formed. The first inner cylinder 51 that has moved on the vibratory table 133a is held between the pair of rails 133b and moves along the rails 133b. During this, the flange part 51a of the first inner cylinder 51 hangs at top part of the rails 133b and thus the first inner cylinder 51 will be in a state of being suspended from the rails 133b. That is, in the case where the first inner cylinder 51 is moved along the rails 133b, attitude of the first inner cylinder 51 will become the attitude in which a leading end of the first inner cylinder 51 is situated above a rear end of the first inner cylinder 51. Then, after passing through a terminal end of the rails 133b, the first inner cylinder 51 is supplied to the inner cylinder pressing part 135 through the tube 134 while keeping such attitude.

The inner cylinder pressing part 135 receives the first inner cylinder 51 that has dropped through the tube 134 and, in the case where the outer cylinder 40 is transported by the transport conveyor 110 in the transport direction to a lower position of the inner cylinder pressing part 135, the inner cylinder pressing part 135 presses the received first inner cylinder 51 downward by a pressing jig 135a. Thus, the first inner cylinder 51 is inserted into the outer cylinder 40 through the leading-end opening 43.

Detailed description of the structure of the second inner cylinder inserting mechanism 132 will be omitted since the second inner cylinder inserting mechanism 132 has a structure substantially similar to that of the first inner cylinder inserting mechanism 131. As shown in FIG. 9, the second inner cylinder inserting mechanism 132 is provided downstream in the transport direction of the transport conveyor 110 than the first inner cylinder inserting mechanism 131. That is to say, after the first inner cylinder 51 is inserted into the outer cylinder 40, the second inner cylinder inserting mechanism 132 inserts the second inner cylinder 52 into the outer cylinder 40.

(4) Tampon Main Body Inserting Mechanism 140

The tampon main body inserting mechanism 140 is a mechanism that inserts the tampon main body 20 into the outer cylinder 40 in which the first inner cylinder 51 and the second inner cylinder 52 are inserted (in other words, assembled applicator 30). It is to be noted that, the tampon main body inserting mechanism 140 inserts the tampon main body 20 through the leading-end opening 43 of the outer cylinder 40 into the outer cylinder 40 from the side including the cord 22. As shown in FIG. 9, the tampon main body inserting mechanism 140 includes a guide tube 141, a drive section 142, a tampon main body pressing part 143 as an example of pressing part, and an air suction device 144.

In this embodiment, the guide tube 141 is a metallic cylindrical body for guiding the tampon main body 20 in the case of inserting the tampon main body 20 into the outer cylinder 40. As shown in FIG. 9, the guide tube 141 is supported by a support member 145 in a state where the longitudinal direction of the guide tube 141 is lying along the vertical direction. In this embodiment, the longitudinal direction of the guide tube 141 is kept so as to constantly align with the vertical direction by the support member 145. And in the case of inserting the tampon main body 20 into the outer cylinder 40, the tampon main body 20 is inserted into the guide tube 141 by other tampon main body inserting mechanism 200. Detail of the guide tube 141 and the other tampon main body inserting mechanism 200 will be explained later on.

The drive section 142 is for moving the guide tube 141 supported by the support member 145 in the vertical direction, by moving the support member 145 in the vertical direction. The drive section 142 moves (lowers) the guide tube 141 toward the outer cylinder 40 in the case where the outer cylinder 40 is transported to the lower position of the guide tube 141 in the transport direction by the transport conveyor 110. As a result, as shown in FIG. 9, the leading-end part of the outer cylinder 40 is fit into a lower-end part of the guide tube 141, and thus the guide tube 141 and the outer cylinder 40 are connected. That is, the drive section 142 connects the guide tube 141 and the outer cylinder 40 by moving the guide tube 141 toward the outer cylinder 40 and inserting the outer cylinder 40 into the guide tube 141 from lower end side (one end side in the longitudinal direction) of the guide tube 141.

The tampon main body pressing part 143 is for pressing the tampon main body 20 inserted into the guide tube 141 by the other tampon main body inserting mechanism 200 downward by a pressing member 143a while the guide tube 141 and the outer cylinder 40 are being connected. That is, the tampon main body pressing part 143 presses the tampon main body 20 inserted into the guide tube 141 so as to insert the tampon main body 20 into the outer cylinder 40 connected to the guide tube 141. The air suction device 144 sucks air from the rear-end side of the outer cylinder 40 (specifically, an opening in the rear-end side of the second inner cylinder 52 inserted into the outer cylinder 40) at the time of inserting the tampon main body 20 into the outer cylinder 40.

In the tampon main body inserting mechanism 140 with above mentioned configuration, in the case where the outer cylinder 40 is transported to the lower position of the guide tube 141 in the transport direction, the drive section 142 lowers the guide tube 141 and thus the guide tube 141 and the outer cylinder 40 are connected. Before connecting the guide tube 141 and the outer cylinder 40, the tampon main body 20 is inserted into the guide tube 141 by the other tampon main body inserting mechanism 200. The guide tube 141 is connected to the outer cylinder 40 while holding the tampon main body 20 inserted by the other tampon main body inserting mechanism 200. In other words, the drive section 142 connects the guide tube 141 and the outer cylinder 40 by moving the guide tube 141 which is in a state of holding the tampon main body 20 inserted by the other tampon main body inserting mechanism 200 toward the outer cylinder 40.

Further, as shown in FIG. 9, the tampon main body 20 inserted into the guide tube 141 is held inside the guide tube 141 in a state where the cotton body 21 is positioned above the cord 22.

When the guide tube 141 and the outer cylinder 40 are connected, the tampon main body pressing part 143 presses the tampon main body 20 inserted into the guide tube 141 downward. More specifically, in the case where the guide tube 141 and the outer cylinder 40 are connected, the tampon main body pressing part 143 inserts the pressing jig 143a into the guide tube 141 from upper end of the guide tube 141, and presses the cotton body 21 of the tampon main body 20 downward by the pressing jig 143a. Thereby, the tampon main body 20 inserted into the guide tube 141 moves inside the guide tube 141. As a result, the tampon main body 20 is inserted into the outer cylinder 40 through the leading-end opening 43 of the outer cylinder 40 connected to the guide tube 141 from the side including the cord 22.

On the other hand, in the case where the tampon main body pressing part 143 presses the tampon main body 20 (that is, in the case where the tampon main body 20 inserted into the guide tube 141 is inserted into the outer cylinder 40), the air suction device 144 sucks air from the rear-end side of the outer cylinder 40. Thus, in the case where the tampon main body 20 moves inside the guide tube 141 toward the outer cylinder 40, the cord 22 of the tampon main body 20 is pulled substantially downwards. As a result, the tampon main body 20 can be inserted into the outer cylinder 40 without slacking the cord 22. And when the tampon main body 20 is accommodated in the outer cylinder 40, the cord 22 is pulled out through the opening at the rear-end side of the second inner cylinder 52 inserted into the outer cylinder 40 (in other words, rear end of the assembled applicator 30).

(5) Bending Mechanism 150

The bending mechanism 150 is a mechanism that performs a bending process on the outer cylinder 40, and the bending process is a pre-process before inserting the inner cylinder 50 and tampon main body 20 into the outer cylinder 40. The bending process is a process for bending each of the plurality of petaloid parts 44 surrounding the leading-end opening 43 of the outer cylinder 40 outwardly in the radial direction of the outer cylinder 40. The bending process is performed for broadening the leading-end opening 43 of the outer cylinder 40 in the case of inserting the inner cylinder 50 and the tampon main body 20 into the outer cylinder 40. By performing the bending process to the outer cylinder 40, the inner cylinder 50 and the tampon main body 20 can be easily inserted into the outer cylinder 40.

The bending mechanism 150 in this embodiment, as shown in FIG. 9, includes a first pusher unit 151, a second pusher unit 152, and a third pusher unit 153. The first pusher unit 151 performs the bending process on the outer cylinder 40 before the first inner cylinder 51 is inserted into the outer cylinder 40. The second pusher unit 152 performs the bending process on the outer cylinder 40 from the time at which the first inner cylinder 51 is inserted into the outer cylinder 40 until the time at which the second inner cylinder 52 is inserted into the outer cylinder 40. The third pusher unit 153 performs the bending process on the outer cylinder 40 from the time at which the second inner cylinder 52 is inserted into the outer cylinder 40 until the time at which the tampon main body 20 is inserted into the outer cylinder 40.

Figure 11A:
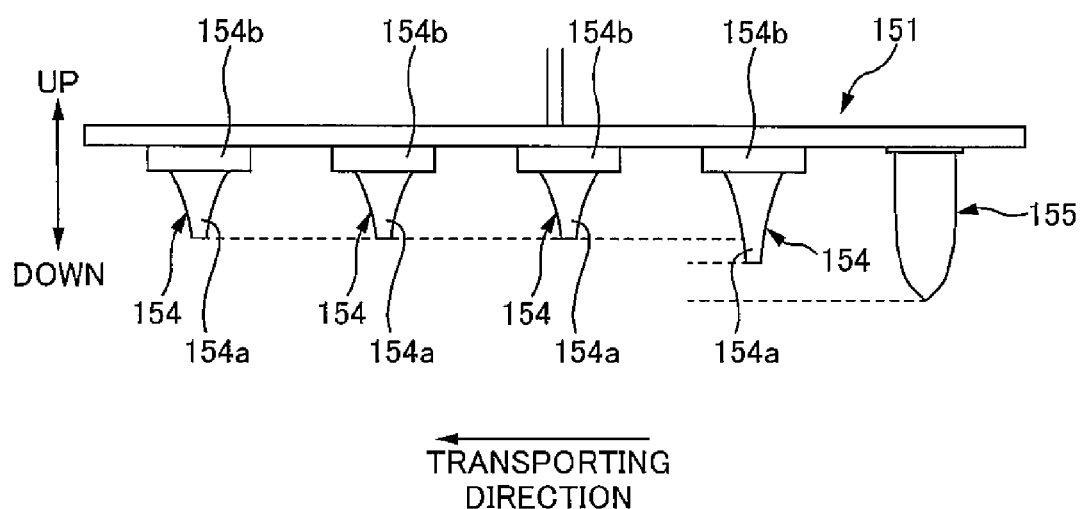
FIG. 11A is a diagram showing a first pusher unit 151.
Figure 11B:
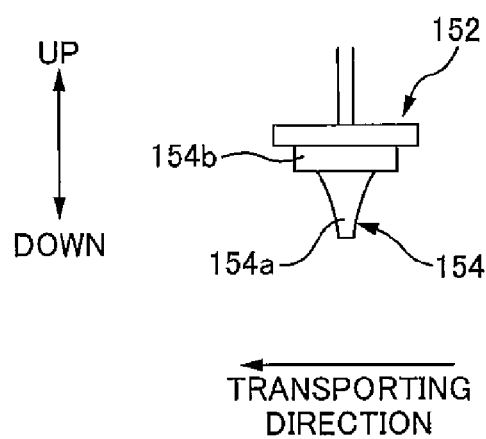
FIG. 11B is a diagram showing a second pusher unit 152.

Each of the first pusher unit 151, the second pusher unit 152, and the third pusher unit 153 includes a pusher 154 as a jig that performs the bending process to the outer cylinder 40 (see FIGS. 11A and 11B). The pusher 154 is a substantially funnel-shaped member. Each of the first pusher unit 151, the second pusher unit 152, and the third pusher unit 153 inserts the pusher 154 into the outer cylinder 40 by lowering the pusher 154 toward the outer cylinder 40 in the case where the outer cylinder 40 is transported to the lower position of the pusher 154 in the transport direction. Thus, the pusher 154 is pushed toward each inner wall surface of the plurality of petaloid parts 44. As a result, each of the plurality of petaloid parts 44 bends in such a manner that it inclines outwardly in the radial direction of the outer cylinder 40.

Hereafter, the bending using the pusher 154 is described in detail by referring to FIGS. 10A to 10D. FIGS. 10A to 10D are explanatory diagrams of the bending process.

The pusher 154 includes a tapered part 154a having a diameter that becomes larger from lower end towards upper end, a disk part 154b adjacent to an upper end portion of the tapered part 154a. The tapered part 154a has substantially a shape of a frustum of a cone. And leading end of the tapered part 154a has a circular flat surface. A diameter of the leading end is shorter than the external diameter of the outer cylinder 40 (specifically, the external diameter of the major diameter part 41) as shown in FIG. 10A. The diameter of rear end of the tapered part 154a is greater than the external diameter of the outer cylinder 40 (specifically, the external diameter of the major diameter part 41). The disk part 154b projects outward than an outer edge of the rear end of the tapered part 154a. That is, the diameter of the disk part 154b is greater than the diameter of the rear end of the tapered part 154a (therefore, greater than the external diameter of the major diameter part 41 of the outer cylinder 40).

In the case where the outer cylinder 40 comes into the lower position of the pusher 154 in the transport direction of the transport conveyor 110, the pusher 154 moves downwardly towards the outer cylinder 40 as shown in FIG. 10A. Thereby, the tapered part 154a of the pusher 154 is inserted into the outer cylinder 40 through the leading-end opening 43 of the outer cylinder 40. Then, an outer peripheral surface of the tapered part 154a comes into contact with each of the inner wall surfaces of the plurality of petaloid parts 44. As a result, as shown in FIG. 10B, each of the plurality of petaloid parts 44 bends in such a manner that it inclines along the outer peripheral surface of the tapered part 154a.

In the case where the tapered part 154a is further inserted into the outer cylinder 40, as shown in FIG. 10C, the disk part 154b of the pusher 154 (specifically, a part that projects outward than the outer edge of the rear end of the tapered part 154a of a lower surface of the disk part 154b) comes into contact with the inner wall surface of each of the plurality of petaloid parts 44. As a result, each of the plurality of petaloid parts 44 will incline substantially at right angles in such a manner that it bends outwardly in the radial direction of the outer cylinder 40. After that, as shown in FIG. 10D, the pusher 154 is moved upward and pulled out of the outer cylinder 40 (in other words, the pusher 154 is separated from each of the plurality of petaloid parts 44).

By performing the bending process to the outer cylinder 40 in above procedure, the outer cylinder 40 (in detail, the rear end of each of the petaloid parts 44) is kept in a bent shape. That is, directly after the bending process, each of the plurality of petaloid parts 44 is in a state where it is inclined outwardly in the radial direction of the outer cylinder 40 at an angle of inclination (an angle shown in symbol θ in FIG. 10D), and it is preferable that the angle of inclination θ is within range from 1 degree to 45 degrees.

As shown in FIG. 11A, the first pusher unit 151 includes the plurality of pushers 154 (in this embodiment, four pushers). FIG. 11A is an enlarged view of the first pusher unit 151 shown in FIG. 9. The first pusher unit 151 performs the bending process on the outer cylinder 40 every time the outer cylinder 40 is positioned below each of the pushers 154. That is, in this embodiment, the bending process is performed a plurality of times (in this embodiment, four times) on the outer cylinder 40 before inserting the first inner cylinder 51 into the outer cylinder 40. On the other hand, as shown in FIG. 11B, each of the second pusher unit 152 and the third pusher unit 153 includes one pusher 154, and performs the bending process on the outer cylinder 40 for only one time. FIG. 11B is an enlarged view of the second pusher unit 152 shown in FIG. 9. Description of the third pusher unit 153 will be omitted since the third pusher unit 153 has same structure as the second pusher unit 152.

Further, the first pusher unit 151 includes another pusher (hereinafter, referred to as auxiliary pusher 155) different from the plurality of pushers 154 as shown in FIG. 11A. The auxiliary pusher 155 includes a substantially conical lower end part as shown in FIG. 11A. The auxiliary pusher 155 is provided at a position upstream of the plurality of pushers 154 in the transport direction of the transport conveyor 110.

The first pusher unit 151 performs process in which the lower end part of the auxiliary pusher 155 is inserted into the outer cylinder 40 and pressed against each inner wall surface of the plurality of petaloid parts 44 in the case where the outer cylinder 40 is positioned below the auxiliary pusher 155 in the transport direction (hereafter, refer to as an auxiliary process) to the outer cylinder 40. That is, the first pusher unit 151 performs the auxiliary process on the outer cylinder 40 before performing the bending process on the outer cylinder 40. And by performing the auxiliary process on the outer cylinder 40, as same as the bending process, each of the plurality of petaloid parts 44 bends in such a manner that it inclines outwardly in the radial direction of the outer cylinder 40.

Hereafter, the object of performing the auxiliary process before the bending process will be explained. At the step of mounting the outer cylinder 40 on the mount 160, there are some cases where the outer cylinder 40 includes the petaloid part 44 inclining inwards. In the case where the bending process is performed on the outer cylinder 40 in a state where the petaloid part 44 is inclining inwards, since the leading end of the tapered part 154*a* of the pusher 154 is a flat surface, the petaloid part 44 may be rolled inward by the leading end of the tapered part 154*a* in the case where the tapered part 154*a* is inserted into the outer cylinder 40. As a result, the petaloid part 44 will be inclined further inwards.

In contrast, a leading-end part (lower end part) of the auxiliary pusher 155 is more pointed than the leading-end part of the tapered part 154*a* of the pusher 154. Therefore, even if the auxiliary pusher 154 is inserted into the outer cylinder 40 with the petaloid part 44 inclining inwards, the leading-end of the auxiliary pusher 154 does not contact the petaloid part 44. That is, even if the lower end part of the auxiliary pusher 155 is inserted into the outer cylinder 40 with the petaloid part 44 inclining inwards, the lower end part of the auxiliary pusher 155 will not roll the petaloid part 44 inwards. And by performing the auxiliary process before the bending process, even if there is the outer cylinder 40 with the petaloid part 44 inclining inwards, it becomes possible to keep the petaloid part 44 open in such a manner that the leading end of the tapered part 154*a* of the pusher 154 does not roll the petaloid part 44 inwards before performing the bending process.

<<Regarding Shape of Guide Tube 141>>

Figure 12A:
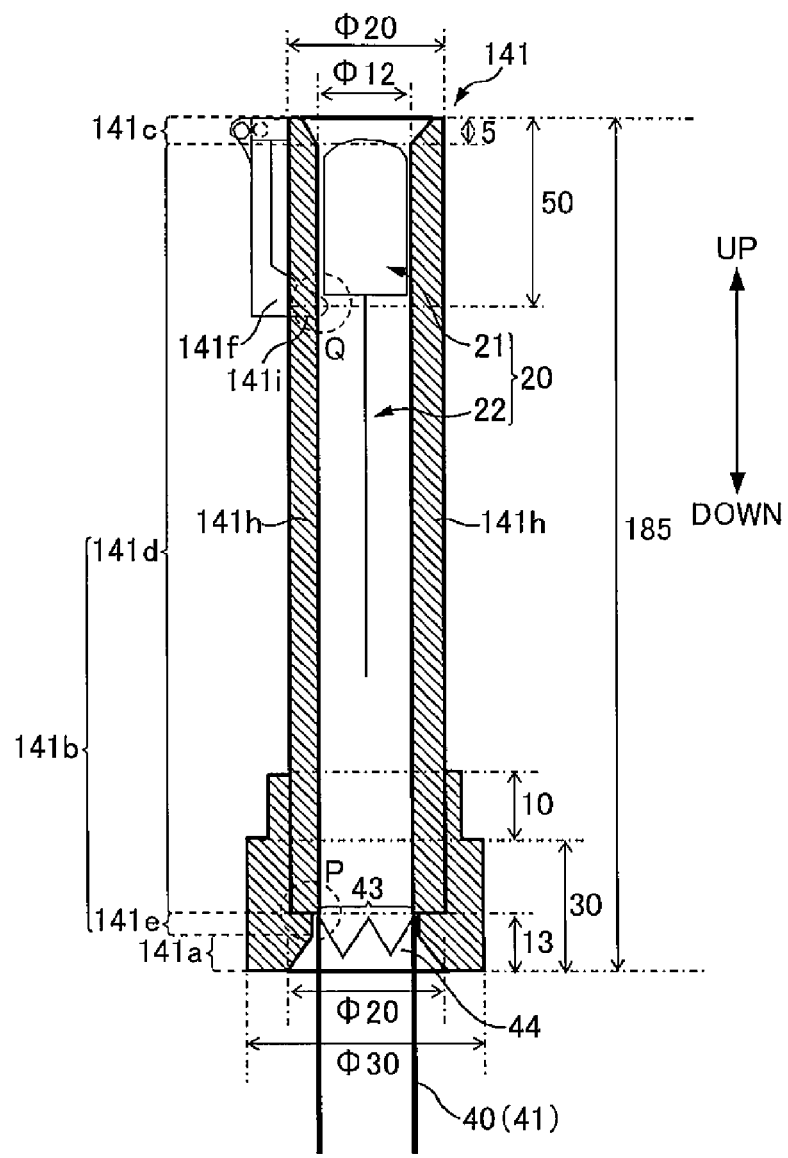
FIG. 12A is a cross-sectional view of a guide tube 141.
Figure 12B:
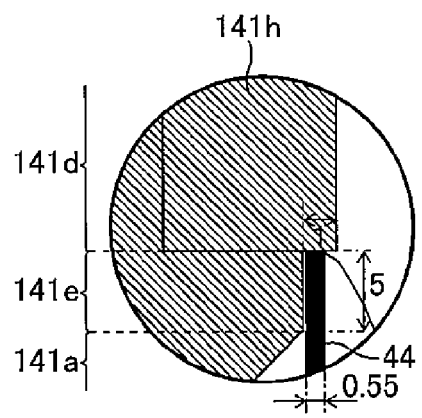
FIG. 12B is an enlarged view of a part shown in symbol "P" in FIG. 12A.
Figure 12C:
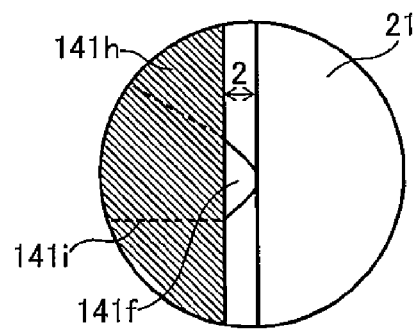
FIG. 12C is an enlarged view of a part shown in symbol "Q" in FIG. 12A.

The shape of the guide tube 141 mentioned above will be explained by referring to FIGS. 12A to 12C. FIG. 12A is a cross-sectional view of the guide tube 141 in which the outer cylinder 40 connected to the guide tube 141 is described together. FIG. 12B is an enlarged view of a part shown in symbol "P" in FIG. 12A. FIG. 12C is an enlarged view of a part shown in symbol "Q" in FIG. 12A, and shows a state in which leading end of a stopper 141*f* is contacting an outer peripheral surface of the cotton body 21 of the tampon main body 20. Further, in FIGS. 12A to 12C, size of each parts of the guide tube 141 is described.

As shown in FIG. 12A, the guide tube 141 includes, from the lower end side (one end side in the longitudinal direction of the guide tube 141), a tapered part 141*a*, a cylindrical part 141*b*, and a broadened part 141*c*. The tapered part 141*a* is a part provided in the lower-end part of the guide tube 141 (one end part in the longitudinal direction of the guide tube 141), and an internal diameter of the tapered part 141*a* becomes smaller from the lower end (one end) of the guide tube 141 toward an upper end (other end). The broadened part 141*c* is a part provided in an upper-end part of the guide tube 141 (other end part in the longitudinal direction of the guide tube 141) and an internal diameter of the broadened part 141*c* becomes larger from the lower end of the guide tube 141 toward the upper end.

The cylindrical part 141*b* is apart provided in a position between the tapered part 141*a* and the broadened part 141*c* in the longitudinal direction of the guide tube 141. That is, the cylindrical part 141*b* is adjacent to the tapered part 141*a* at the upper-end side (other end side) of the tapered part 141*a*. The cylindrical part 141*b* includes a first cylindrical part 141*d* and a second cylindrical part 141*e* with larger internal diameter than the first cylindrical part 141*d* as shown in FIG. 12A. The second cylindrical part 141*e* is provided in a position between the first cylindrical part 141*d* and the tapered part 141*a* in the longitudinal direction of the guide tube 141. Further, difference between the internal diameter of the first cylindrical part 141*d* and the second cylindrical part 141*e* is about 2 mm (for example, refer to FIG. 12B).

As shown in FIG. 12A, the first cylindrical part 141*d* is a part that holds the tampon main body 20 inserted into the guide tube 141 by the other tampon main body inserting mechanism 200. The internal diameter of the first cylindrical part 141*d* is made slightly larger than the diameter of the tampon main body 20 (specifically about 12 mm). The tampon main body 20 held inside the guide tube 141 is pressed by the tampon main body pressing part 143 and thus moves slidingly inside the first cylindrical part 141*d*. In other words, the tampon main body pressing part 143 presses the tampon main body 20 so that the tampon main body 20 held inside the guide tube 141 moves inside the first cylindrical part 141*d*.

Further, as shown in FIG. 12A, in the embodiment, the length of the first cylindrical part 141*d* of the guide tube 141 in the longitudinal direction is a length that can contain the tampon main body 20 in a state where the cord 22 is extended. That is, the length of the guide tube 141 in the longitudinal direction according to the embodiment is sufficiently longer than the length from the leading end to the rear end of the tampon main body 20 in a state where the cord 22 is extended (specifically about 185 mm).

The second cylindrical part 141*e* is a part where the leading-end part of the outer cylinder 40 is caught, in the case where the drive section 142 connects the guide tube 141 and the outer cylinder 40. That is, in the embodiment, the leading-end part of the outer cylinder 40 is caught in the second cylindrical part 141e and thus the guide tube 141 is connected to the outer cylinder 40.

As shown in FIG. 12A, the upper-end side of the guide tube 141 includes the hook-shaped stopper 141f. The stopper 141f is for holding the tampon main body 20 inserted into the guide tube 141 by the other tampon main body inserting mechanism 200 inside the guide tube 141 (specifically, inside the first cylindrical part 141d).

As shown in FIG. 12A, the stopper 141f is provided in the upper-end side of an outer peripheral part 141h of the guide tube 141 so as to rotate about a rotation axis 141g. Further, an approach hole 141i for approaching a leading-end part of the stopper 141f into the guide tube 141 is formed in the outer peripheral part 141h (specifically the first cylindrical part 141d). The stopper 141f locks the tampon main body 20 (more specifically, rear end of the cotton body 21) inserted into the guide tube 141 in a state where the leading-end of the stopper 141f is approaching into the guide tube 141 through the approach hole 141i. Thereby the tampon main body 20 inserted into the guide tube 141 is held inside the guide tube 141 until it is pressed by the tampon main body pressing part 143.

<<Regarding Other Tampon Main Body Inserting Mechanism 200>>

Figure 13:
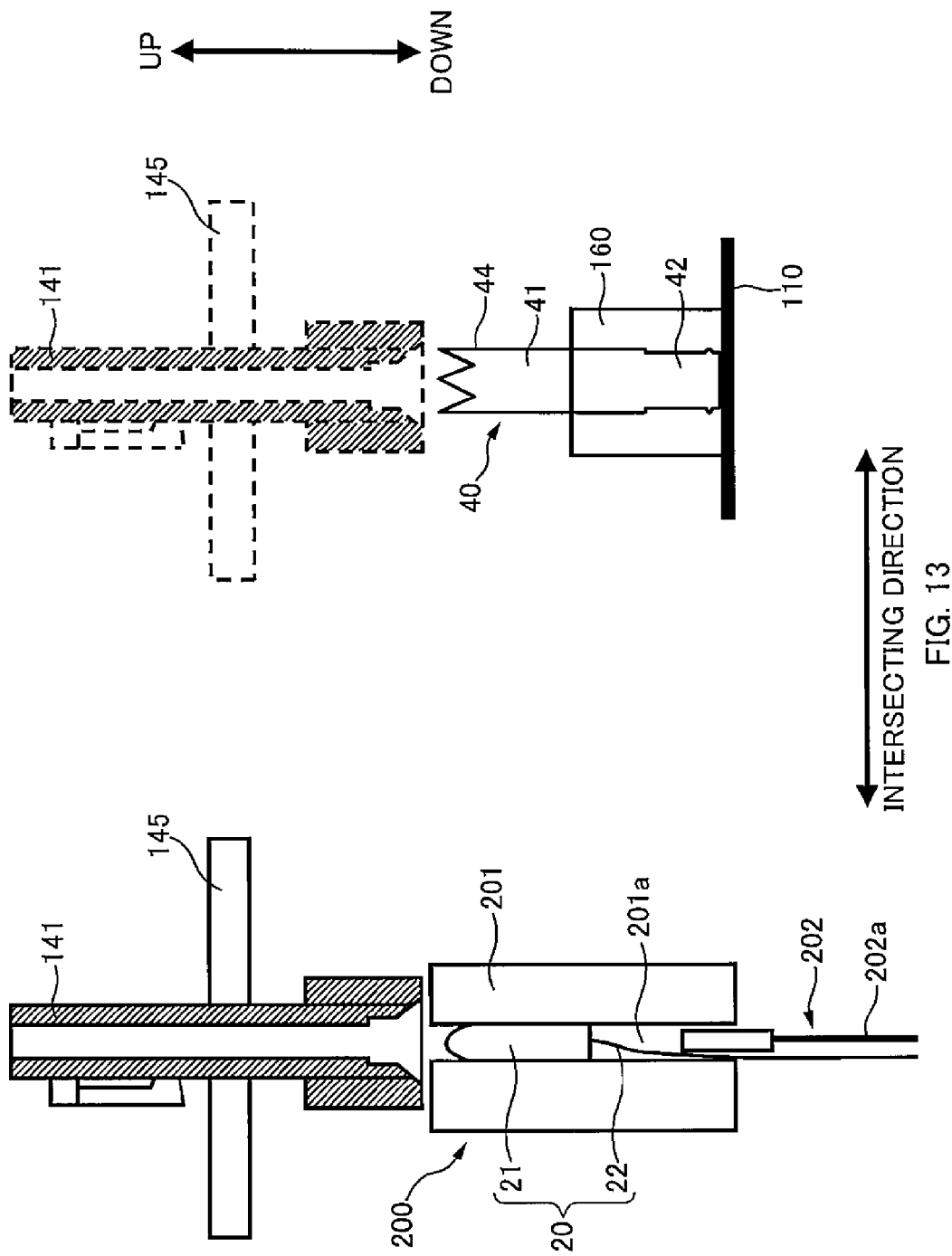
FIG. 13 is a schematic diagram of other tampon main body inserting mechanism 200.

The other tampon main body inserting mechanism 200 will be described by referring to FIG. 13. FIG. 13 is a schematic diagram of the other tampon main body inserting mechanism 200. Further, the vertical direction and a direction that intersects the transport direction of the transport conveyor 110 in a horizontal direction (hereinafter, intersecting direction) are shown by arrows in FIG. 13.

The other tampon main body inserting mechanism 200 is provided in a position distanced from the transport conveyor 110 in the horizontal direction. As shown in FIG. 13, the other tampon main body inserting mechanism 200 includes a holder 201 for holding the tampon main body 20, and other tampon main body pressing part 202 that presses the tampon main body 20 held inside the holder 201 and thereby inserts the tampon main body 20 into the guide tube 141.

As shown in FIG. 13, the holder 201 includes a throughhole 201a that penetrates the holder 201 along the vertical direction. The tampon main body 20 is inserted into the throughhole 201a by an inserting mechanism not shown. The holder 201 holds the tampon main body 20 inserted into the throughhole 201a inside the throughhole 201a. The holder 201 stands so that the longitudinal direction of the throughhole 201a is along the vertical direction in the case where the tampon main body 20 held by the holder 201 is inserted into the guide tube 141. More in detail, the holder 201 stands so that the cord 22 of the tampon main body 20 held by the holder 201 hangs substantially directly downwards.

The other tampon main body pressing part 202 presses a pressing jig 202a upward in the case where the holder 201 is standing in above mentioned state. In here, the guide tube 141 is in a state where the longitudinal direction thereof is along the vertical direction, and the rear-end opening of the guide tube 141 is facing an upper-end opening of the throughhole 201a (that is, a state shown in FIG. 13). In such state, the other tampon main body pressing part 202 presses the tampon main body 20 upward inside the throughhole 201a. Thereby the tampon main body 20 held by the holder 201 is inserted into the guide tube 141 from the cotton body 21 side (that is, opposite side of the side including the cord 22) from downside of the guide tube 141.

Next, a procedure for inserting the tampon main body 20 into the guide tube 141 by the other tampon main body inserting mechanism 200 of forementioned structure will be explained.

By the other tampon main body inserting mechanism 200 inserting the tampon main body 20 into the guide tube 141, the guide tube 141 positioned in upper position of the transport conveyor 110 moves to upper position of the other tampon main body inserting mechanism 200 in the intersecting direction. That is, as shown in FIG. 13, the guide tube 141 can reciprocate between the upper position of the transport conveyor 110 and the upper position of the other tampon main body inserting mechanism 200 in the intersecting direction. The reciprocating movement of the guide tube 141 in the intersecting direction is performed by other drive section (not shown).

And in the state where the guide tube 141 is positioned in the upper position of the other tampon main body inserting mechanism 200, and the rear-end opening of the guide tube 141 is facing the upper-end opening of the throughhole 201a, the tampon main body 20 inserted into the throughhole 201a beforehand is pressed upward by the other tampon main body pressing part 202. Thus the tampon main body 20 moves inside the throughhole 201a and is inserted into the guide tube 141 from the rear-end opening of the guide tube 141. In such case, as described before, the tampon main body 20 is inserted into the guide tube 141 from the cotton body 21 side.

As described above, the other tampon main body inserting mechanism 200 inserts the tampon main body 20 from the opposite side of the side including the cord 22 into the guide tube 141 from downside of the guide tube 141. The tampon main body 20 is pressed by the other tampon main body pressing part 202 until it reaches the position where the tampon main body 20 is locked by the stopper 141f. Thereby, the tampon main body 20 is held in the guide tube 141 (specifically, the first cylindrical part 141d). The tampon main body 20 is held in the guide tube 141 in a state where the cord 22 is hanging substantially directly downward. As described before, the tampon main body 20 is held in the guide tube 141 so as to be contained from its leading end to rear end inside the first cylindrical part 141d.

By above procedure, the tampon main body 20 is inserted and thus held inside the guide tube 141. In present embodiment, as mentioned before, the tampon main body 20 is inserted into the guide tube 141 from the opposite side of the side including the cord 22 (the cotton body 21 side). Supposing that the tampon main body 20 is inserted into the guide tube 141 from the side including the cord 22, measures for straightly extending the cord 22 by sucking the cord 22 etc. needs to be taken. On the other hand, above measures does not have to be taken if the tampon main body 20 is inserted into the guide tube 141 from the cotton body 21 side. That is, in the case where the tampon main body 20 is inserted into the guide tube 141 by following above procedure, the cord 22 hangs substantially directly downward by its own weight. That is, the tampon main body 20 can be inserted into the guide tube 141 with its cord extended.

After that, at the time in which the tampon main body 20 is held in the guide tube 141, the guide tube 141 moves towards the upper position of the transport conveyor 110 in the intersecting direction. That is, the guide tube 141 moves, in a state of holding the tampon main body 20, to the position where the rear-end opening of the guide tube 141 faces the leading-end opening 43 of the outer cylinder 40.

<<Regarding Detailed Process of Inserting Tampon Main Body 20 into Outer Cylinder 40>>

In the case where the outer cylinder 40 is transported to the lower position of the guide tube 141 in the transport direction, process of inserting the tampon main body 20 into the outer cylinder 40 is performed by the tampon main body inserting mechanism 140. Hereafter, the process is described in detail.

Before performing the process of inserting the tampon main body 20 into the outer cylinder 40 (more specifically, before the outer cylinder 40 is transported to the lower position of the guide tube 141 in the transport direction), the other tampon main body inserting mechanism 200 inserts the tampon main body 20 into the guide tube 141 by above procedure. The inserted tampon main body 20 is locked by the stopper 141f and held in the guide tube 141. That is, the guide tube 141 keeps waiting in the upper position of the transport conveyer 110 in the state of holding the tampon main body 20 until the outer cylinder 40 is transported to the lower position of the guide tube 141.

On the other hand, while the outer cylinder 40 is being transported to the lower position of the guide tube 141, the mentioned bending mechanism 150 performs the bending process to the outer cylinder 40.

Specifically describing, each of the first pusher unit 151, the second pusher unit 152, and the third pusher unit 153 performs the bending process to the outer cylinder 40 at the time of which the outer cylinder 40 is positioned in the lower position of the pusher 154 provided to each of the unit. The first pusher unit 151 performs the pre-process to the outer cylinder 40 by using the auxiliary pusher 155 before the bending process. The outer cylinder 40 on which the pre-process is performed reaches the lower position of the guide tube 141 in a bent shape (that is, in a state where each of the plurality of petaloid parts 44 is inclined outwardly in the radial direction of the outer cylinder 40). After that, a process of inserting the tampon main body 20 into the outer cylinder 40 on which the bending process is performed is performed.

Figure 14:
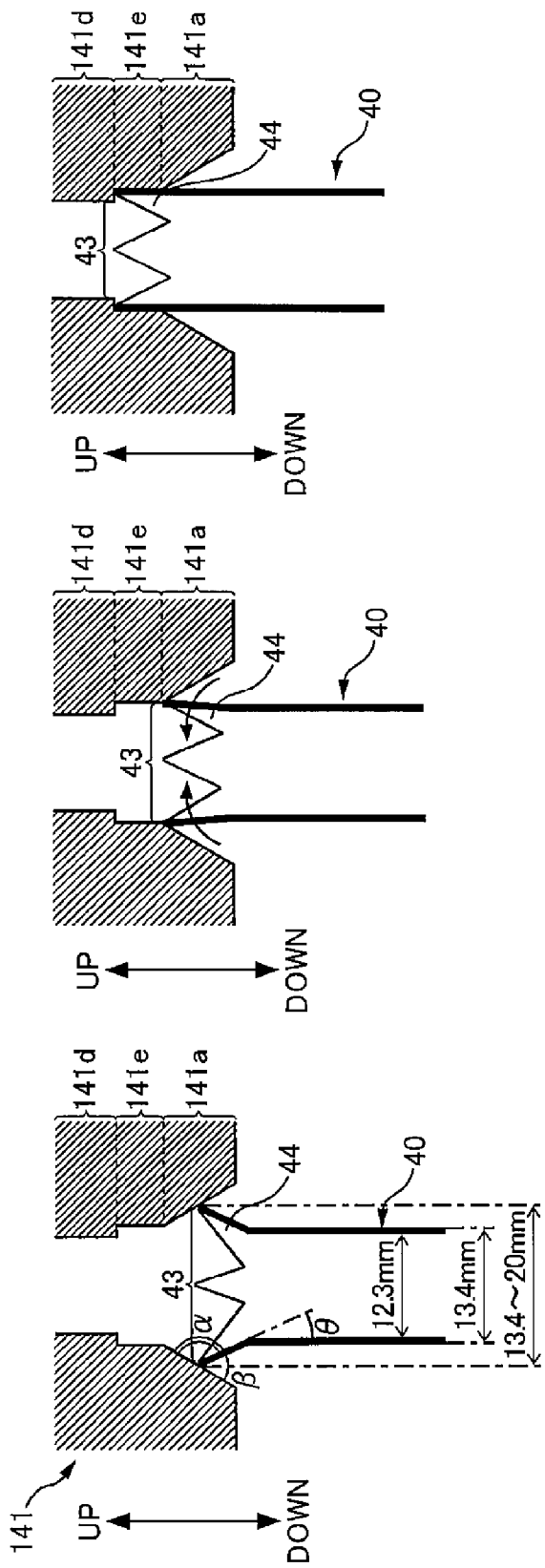
FIGS. 14A to 14C are explanatory diagrams showing how the outer cylinder 40 and the guide tube 141 are connected.

In the process of inserting the tampon main body 20 into the outer cylinder 40, firstly, process of connecting the outer cylinder 40 on which the pre-process is performed and the guide tube 141 is performed. In this process, by the drive section 142 lowering the guide tube 141 toward the outer cylinder 40 on which the bending process is performed, the leading-end part of the outer cylinder 40 is inserted into the guide tube 141 from the lower end side (one end side in the longitudinal direction) of the guide tube 141. Thereby, the guide tube 141 connects to the outer cylinder 40. Here, a process of connecting the guide tube 141 and the outer cylinder 40 is explained by referring to FIGS. 14A to 14C. FIGS. 14A to 14C are explanatory diagrams showing the process of connecting the guide tube 141 and the outer cylinder 40.

First, the drive section 142 lowers the guide tube 141 towards the outer cylinder 40 on which the bending process is performed, as shown in FIG. 14A, the leading end of the petaloid part 44 of the outer cylinder 40 contacts the inner peripheral surface of the tapered part 141a. At this time, as shown in FIG. 14A, the petaloid part 44 contacts the inner peripheral surface of the tapered part 141a in a state where it is inclined outwardly at the angle of inclination θ.

By further lowering the guide tube 141 from above state, the leading-end part of the outer cylinder 40 moves toward the upper end of the guide tube 141 inside the tapered part 141a. At this time, the leading end of the petaloid part 44 keeps on contacting the inner peripheral surface of the tapered part 141a as shown in FIG. 14B. As a result, the leading-end part of the outer cylinder 40 moves toward the cylindrical part 141b (more specifically, second cylindrical part 141e) inside the tapered part 141a. That is, the guide tube 141 guides the leading-end part of the outer cylinder 40 into the cylindrical part 141b by the leading end of the petaloid part 44 contacting the inner peripheral surface of the tapered part 141a at the time of inserting the outer cylinder 40 into the guide tube 141. As a result, the leading-end part of the outer cylinder 40 is smoothly inserted into the guide tube 141.

Here, for the guide tube 141 appropriately guiding the leading-end part of the outer cylinder 40 into the cylindrical part 141b, the petaloid part 44 needs to contact the inner peripheral surface of the tapered part 141a at the appropriate contact angle. Specifically describing, of two angles formed by the inner peripheral surface of the tapered part 141a and the petaloid part 44 contacting the inner peripheral surface, an angle on upper side seen from the petaloid part 44 (an angle shown in symbol α in FIG. 14A), needs to be larger than an angle on lower side (an angle shown in symbol β in FIG. 14A). In consideration of such matter, the bending process needs to be performed so as to make the mentioned angle of inclination θ an appropriate angle. As mentioned before, it is preferable that the angle of inclination θ is within the range from 1 degree to 45 degrees. In the case where the petaloid part 44 is inclined at the angle of inclination θ within the range, the petaloid part 44 can contact the inner peripheral surface of the tapered part 141a at the appropriate contact angle.

By lowering the guide tube 141 while the leading end of the petaloid part 44 contacts the inner peripheral surface of the tapered part 141a, the leading-end part of the outer cylinder 40 moves inside the tapered part 141a, and thus the petaloid part 44 bent by inclining outward will gradually follow the longitudinal direction of the outer cylinder 40 as shown in FIG. 14B. This is because the internal diameter of the tapered part 141a becomes smaller from lower end to upper end of the guide tube 141. That is, the angle of inclination θ of the petaloid part 44 is regulated by the inner peripheral surface of the tapered part 141a and lessens as the outer cylinder 40 moves inside the tapered part 141a.

After that, by further lowering the guide tube 141, the leading-end part of the outer cylinder 40 enters the second cylindrical part 141e. And as shown in FIG. 14C, the guide tube 141 will be lowered until the leading end of the outer cylinder 40 (in other words, the leading end of the petaloid part 44) reaches a stepped part between the inner peripheral surface of the second cylindrical part 141e and the inner peripheral surface of the first cylindrical part 141d. By the leading end of the outer cylinder 40 reaching the stepped part between the inner peripheral surface of the second cylindrical part 141e and the inner peripheral surface of the first cylindrical part 141d, as shown in FIG. 14C, the leading end part of the outer cylinder 40 is caught in the second cylindrical part 141e. As a result, the guide tube 141 is connected appropriately to the outer cylinder 40.

Further, in the case where the leading end part of the outer cylinder 40 is caught in the second cylindrical part 141e, each of the plurality of petaloid parts 44 contacts the inner peripheral surface of the second cylindrical part 141e and is along the longitudinal direction of the outer cylinder 40. And each of the plurality of petaloid parts 44 contacts the inner peripheral surface of the second cylindrical part 141e. Specifically explaining, due to the bending process the outer cylinder 40 is kept in a bent shape in which the petaloid part 44 is bent by inclining outwardly. On the other hand, the inner peripheral surface of the second cylindrical part 141e regulates bending of the petaloid part 44. Therefore, the petaloid part 44 comes into contact with the inner peripheral surface of the second cylindrical part 141e at an outer wall face thereof. As a result, in the state where the guide tube 141 and the outer cylinder 40 are connected, the leading-end opening 43 of the outer cylinder 40 is kept in an opened state.

As above, by fitting the leading-end part of the outer cylinder 40 into the second cylindrical part 141e, the guide tube 141 is connected to the outer cylinder 40 by contacting the petaloid part 44 at the inner peripheral surface of the second cylindrical part 141e. In other words, the drive section 142 moves the guide tube 141 towards the outer cylinder 40 and makes the guide tube 141 contact the leading-end part of the outer cylinder 40, and thereby connects the guide tube 141 and the outer cylinder 40. And while the guide tube 141 and the outer cylinder 40 are being connected, the leading-end opening 43 of the outer cylinder 40 is kept in an opened state.

Further, in the case where the guide tube 141 and the outer cylinder 40 are connected, the tampon main body 20 held in the guide tube 141 is in a state of being contained from its upper end to rear end (that is, the entire tampon main body 20) inside the first cylindrical part 141d. This is, as described before, the length of the guide tube 141 in the longitudinal direction is sufficiently longer than the length from the leading end to the rear end of the tampon main body 20 in a state where the cord 22 is extended. In this way, the guide tube 141 and the outer cylinder 40 are connected without the cord 22 of the tampon main body 20 held in the guide tube 141 touching the petaloid part 44 of the outer cylinder 40.

Further, in a case where the leading-end part of the outer cylinder 40 is caught in the second cylindrical part 141e, the petaloid part 44 contacting the inner peripheral surface of the second cylindrical part 141e is positioned outward than the inner peripheral surface of the first cylindrical part 141d in the radial direction of the guide tube 141 (refer to FIG. 12B). In other words, the inner peripheral surface of the first cylindrical part 141d is positioned inward than the petaloid part 44 contacting the inner peripheral surface of the second cylindrical part 141e in the radial direction of the guide tube 141. This is because the thickness of the petaloid part 44 (that is, the thickness of the outer cylinder 40 that is about 0.55 mm in the embodiment) is smaller than the stepped part between the inner peripheral surface of the first cylindrical part 141d and the inner peripheral surface of the second cylindrical part 141e (about 1 mm in the embodiment).

After connecting the guide tube 141 and the outer cylinder 40, a process of pressing the tampon main body 20 inserted into the guide tube 141 downward is performed by the tampon main body pressing part 143. By above process, the tampon main body 20 is inserted into the outer cylinder 40 connected to the guide tube 141. That is, the tampon main body 20 held in the guide tube 141 moves inside the first cylindrical part 141d toward the leading-end opening 43 of the outer cylinder 40 by placing the side including the cord 22 forward.

At this time, the tampon main body 20 is inserted into the outer cylinder 40 by moving inside the first cylindrical part 141d without contacting the cord 22 with the petaloid part 44 of the outer cylinder 40. This is because, in the state where the guide tube 141 and the outer cylinder 40 are connected, the petaloid part 44 contacting the inner peripheral surface of the second cylindrical part 141e is positioned outward than the inner peripheral surface of the first cylindrical part 141d in the radial direction of the guide tube 141. As a result, the tampon main body 20 held in the guide tube 141 can be inserted into the outer cylinder 40 connected to the guide tube 141 without the cord 22 being caught by the petaloid part 44.

Further, the tampon main body 20 is pressed onto the inner peripheral surface of the guide tube 141 (specifically, the inner peripheral surface of the first cylindrical part 141d) while being pressed by the leading-end part of the stopper 141f, at the time of passing the position in which the approach hole 141i is formed in the longitudinal direction of the guide tube 141 (refer to FIG. 12C). As a result, at the time of the tampon main body 20 moving inside the first cylindrical part 141d, a gap is formed between the tampon main body 20 (specifically, the cotton body 21) and the inner peripheral surface of the first cylindrical part 141d.

On the other hand, in the case where the tampon main body pressing part 143 presses the tampon main body 20 (in the case where the tampon main body 20 inserted into the guide tube 141 is inserted into the outer cylinder 40), a process of sucking air through the rear-end side of the outer cylinder 40 is performed by the air suction device 144. As forementioned, this process is performed so as to prevent the cord 22 of the tampon main body 20 from slacking at the time of inserting the tampon main body 20 into the guide tube 141. The process will be described in detail.

In the case where the guide tube 141 and the outer cylinder 40 are connected, the air suction device 144 starts sucking air through the rear-end side of the outer cylinder 40. Thereby, an air inside the guide tube 141 flows toward the air suction device 144, and an air outside the guide tube 141 flows into the guide tube 141 through the approach hole 141i. The air flowed into the guide tube 141 flows so as to pass through the gap formed between the inner peripheral surface of the first cylindrical part 141d and the tampon main body 20. As a result, an air flow running from upward to downward is generated inside the guide tube 141 and the outer cylinder 40 connected to each other.

By the forementioned air flow, the cord 22 of the tampon main body 20 extends so as to be pulled substantially directly downward. That is, at the time of inserting the tampon main body 20 inserted into the guide tube 141 into the outer cylinder 40, the air suction device 144 sucks air so that the cord 22 of the tampon main body 20 extends straightly toward the leading-end opening 43 of the outer cylinder 40. As a result, the tampon main body 20 is inserted properly into the outer cylinder 40 from the side including the cord 22.

By above series of processes, the tampon main body 20 inserted into the guide tube 141 is properly inserted into the outer cylinder 40 connected to the guide tube 141 from the side including the cord 22. After the tampon main body 20 is inserted into the outer cylinder 40, the guide tube 141 and the outer cylinder 40 are separated from each other by the drive section 142 moving the guide tube 141 upward. Also, the outer cylinder 40 released from connection with the guide tube 141 is transported to a process for performing the leading-end processing by the transport conveyor 110 (refer to FIG. 9).

===Regarding Efficiency of Assembling Apparatus 100 According to the Embodiment===

In the assembling apparatus 100 according to the embodiment, at inserting the tampon main body 20 inserted into the guide tube 141 into the outer cylinder 40, the guide tube 141 and the outer cylinder 40 are connected by contacting the guide tube 141 to the leading-end part of the outer cylinder 40. In such state, while sucking air from the rear-end side of the outer cylinder 40 the tampon main body 20 is inserted into the outer cylinder 40 from the side including the cord 22 through the leading-end opening 43. Thereby, in the embodiment, the tampon main body 20 can be properly inserted into the outer cylinder 40.

That is, as described in "Problem to be solved by the invention", in a state where the guide tube 141 and the outer cylinder 40 are separated from each other, it is difficult to insert the tampon main body 20 that is inserted into the guide tube 141 into the outer cylinder 40 from the side including the cord 22. That is, the petaloid part 44 of the outer cylinder 40 is exposed in a state where the guide tube 141 and the outer cylinder 40 are separated from each other. In the state where the petaloid part 44 is exposed, the cord 22 of the tampon main body 20 is likely to touch the petaloid part 44 at the time of passing the leading-end opening 43 surrounded by the petaloid parts 44.

Figure 15:
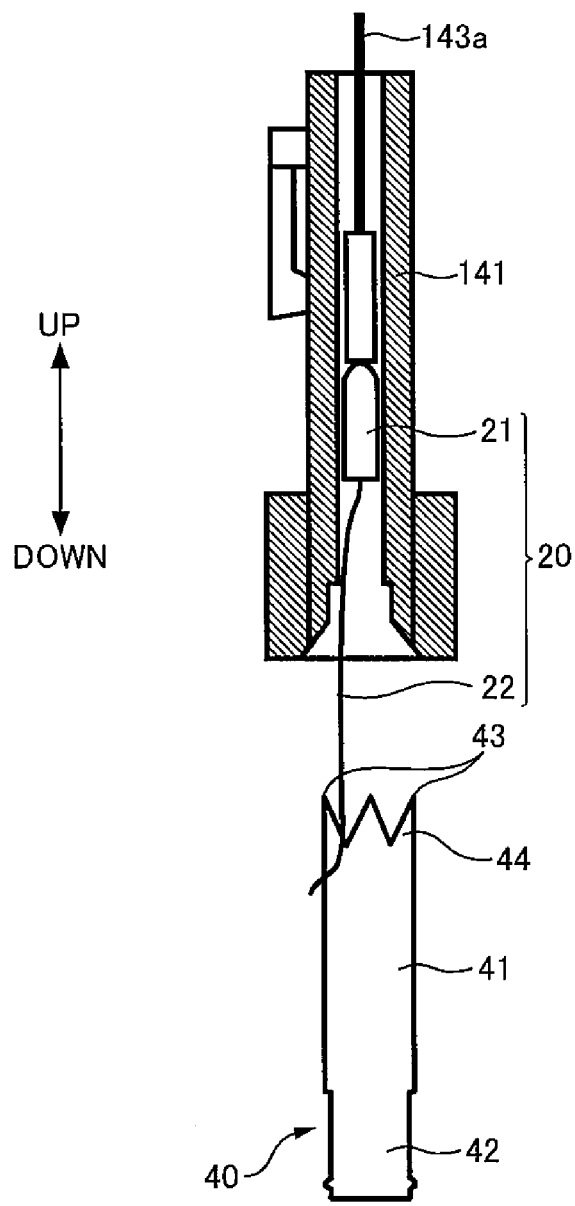
FIG. 15 is an explanatory diagram of problems to be solved by the assembling apparatus 100 of the embodiment.

And in the case where the tampon main body 20 that is inserted into the guide tube 141 is inserted into the outer cylinder 40 from the side including the cord 22, in a state where the cord 22 is likely to touch the petaloid part 44, the cord 22 could be caught by the petaloid part 44 as shown in FIG. 15. FIG. 15 is a diagram showing a state in which the cord 22 is caught by the petaloid part 44. In the case where the cord 22 is caught by the petaloid part 44 like this, the tampon main body 20 cannot be inserted properly into the outer cylinder 40.

On the other hand, in the embodiment, the tampon main body 20 is inserted into the outer cylinder 40 in a state where the guide tube 141 contacts the petaloid part 44 of the outer cylinder 40 and thus the guide tube 141 and the outer cylinder 40 are connected. That is, in the embodiment, at the time of inserting the tampon main body 20 into the outer cylinder 40, contact between the petaloid part 44 and the cord 22 is regulated because the petaloid part 44 is not exposed. As a result, the tampon main body 20 inserted into the guide tube 141 can be properly inserted into the outer cylinder 40 without the cord 22 being caught by the petaloid part 44.

Further, in the embodiment, the tampon main body 20 that is inserted into the guide tube 141 is inserted into the outer cylinder 40 through the first cylindrical part 141d. On the other hand, in the state where the guide tube 141 and the outer cylinder 40 are connected, the petaloid part 44 is contacting the inner peripheral surface of the second cylindrical part 141e, and is positioned outward than the inner peripheral surface of the first cylindrical part 141d in the radial direction of the guide tube 141. Therefore, in the case of inserting the tampon main body 20 into the outer cylinder 40, contact between the petaloid part 44 and the cord 22 is regulated. As a result, the tampon main body 20 moves inside the first cylindrical part 141d without the cord 22 being caught by the petaloid part 44 and is inserted into the outer cylinder 40.

===Modification Example of Shape of Guide Tube 141===

Figure 16A:
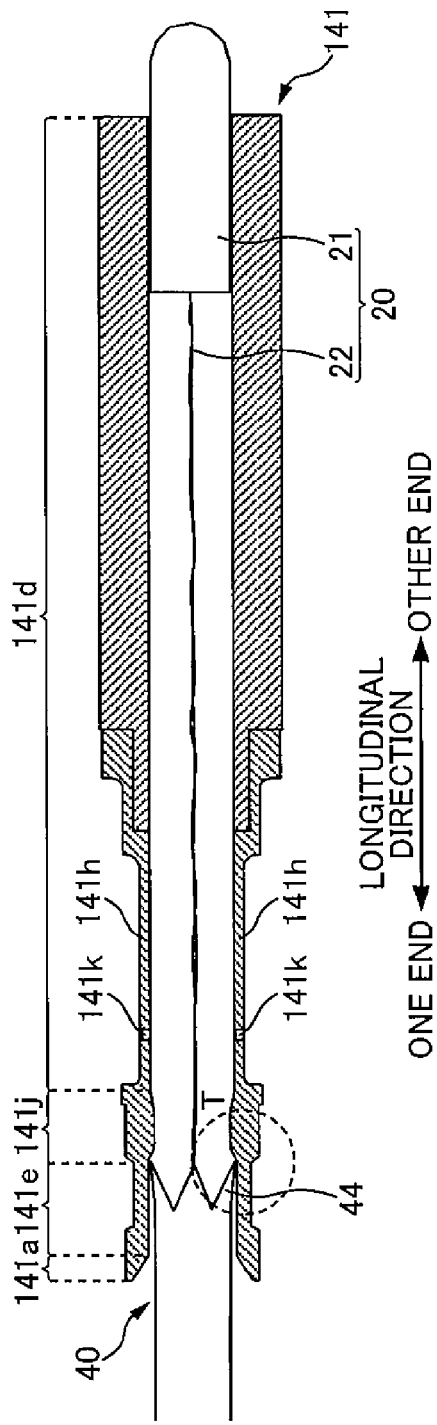
FIG. 16A is a diagram showing a guide tube 141 according to first modification example.
Figure 16B:
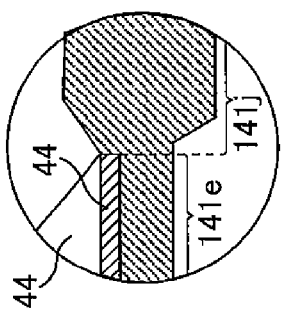
FIG. 16B is an enlarged view of a part shown in symbol "T" in FIG. 16A.
Figure 17A:
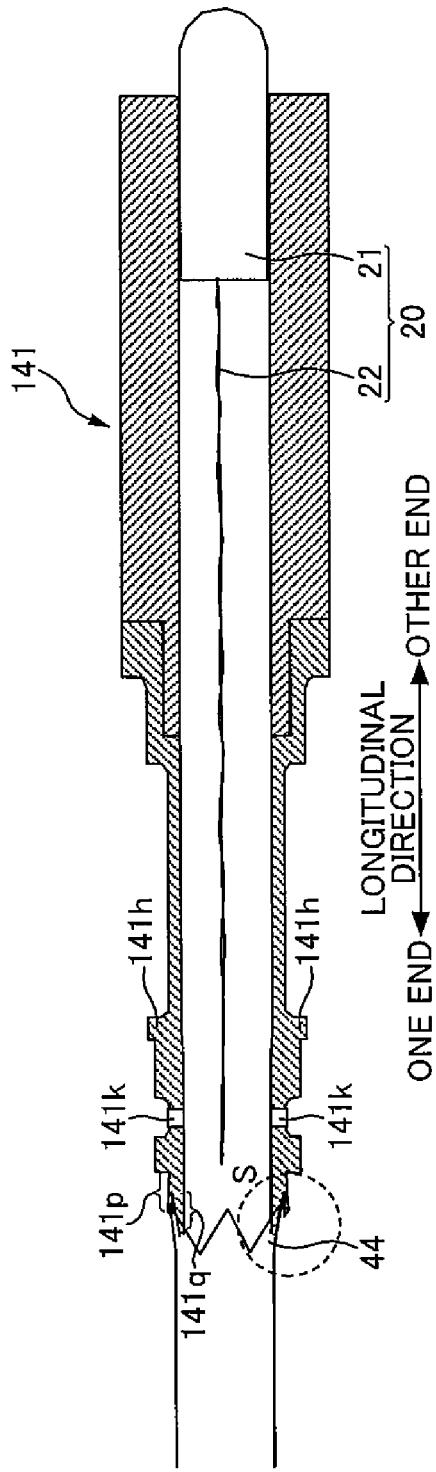
FIG. 17A is a diagram showing a guide tube 141 according to second modification example.
Figure 17B:
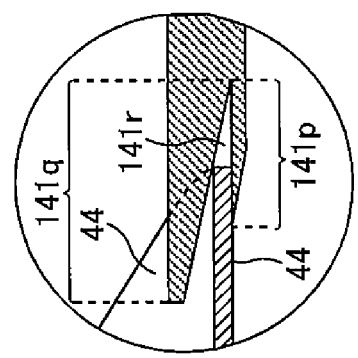
FIG. 17B is an enlarged view of a part shown in symbol "S" in FIG. 17A.

Shape of the guide tube 141 is not limited to the shape of above embodiment, and for example, a shape shown in FIGS. 16A and 16B (hereafter, a first modification example) or a shape shown in FIGS. 17A and 17B (hereafter, a second modification example) is possible. FIG. 16A is a diagram showing a guide tube 141 according to the first modification example. FIG. 16B is an enlarged view of a part shown by symbol "T" in FIG. 16A. FIG. 17A is a diagram showing a guide tube 141 according to the second modification example. FIG. 17B is an enlarged view of a part shown by symbol "S" in FIG. 17A. Hereafter, the modification examples of shape of the guide tube 141 will be described.

<<Regarding First Modification Example>>

As shown in FIG. 16A, the guide tube 141 according to the first modification example is connected to the outer cylinder 40 by inserting the leading-end part of the outer cylinder 40 into a one end part in the longitudinal direction of the guide tube 141. As shown in FIG. 16A, the guide tube 141 according to the first modification example includes a tapered part 141a, a first cylindrical part 141d, and a second cylindrical part 141e. Further, the guide tube 141 according to the first modification example includes a constricted part 141j with constricted inner surface at a position between the first cylindrical part 141d and the second cylindrical part 141e. An internal diameter of each part of the constricted part 141j is smaller than the internal diameter of the first cylindrical part 141d and the second cylindrical part 141e.

The guide tube 141 according to the first modification example is connected to the outer cylinder 40 by the leading-end part of the outer cylinder 40 being caught in the second cylindrical part 141e. And the guide tube 141 according to the first modification example, in the state of being connected to the outer cylinder 40, contacts the petaloid part 44 of the outer cylinder 40 at the inner peripheral surface of the second cylindrical part 141e. Further, as shown in FIG. 16B, the petaloid part 44 contacting an inner peripheral surface of the second cylindrical part 141e is positioned outward than an inner peripheral surface of the constricted part 141j in the radial direction of the guide tube 141. As a result, in the case where the tampon main body 20 is inserted into the outer cylinder 40, contact between the petaloid part 44 and the cord 22 will be regulated. Therefore, the tampon main body 20 is inserted into the outer cylinder 40 by moving inside the guide tube 141 according to the first modification example without the cord 22 being caught by the petaloid part 44.

Further, the guide tube 141 according to the first modification example has an internal diameter substantially equal to a diameter of the tampon main body 20 inserted into the guide tube 141 by the other tampon main body inserting mechanism 200. That is, the tampon main body 20 inserted into the guide tube 141 according to the first modification example contacts deeply with an inner peripheral surface of the guide tube 141. And the guide tube 141 according to the first modification example holds the tampon main body 20 so that a leading-end part of the cotton body 21 exposes from other end in the longitudinal direction of the guide tube 141 as shown in FIG. 16A.

Further, the guide tube 141 according to the first modification example includes an airhole 141k formed at one end side in the longitudinal direction of an outer peripheral part 141h of the guide tube 141. By providing the airhole 141k, forementioned air flow is generated properly when the air suction device 144 operates in a state where the guide tube 141 according to the first modification example and the outer cylinder 40 are connected. Hereafter, the reason why the airhole 141k is included is explained.

As forementioned, the inner peripheral surface in the other end side in the longitudinal direction of the guide tube 141 according to the first modification example contacts closely with the tampon main body 20 held in the guide tube 141. To put it briefly, the opening in the other end side in the longitudinal direction of the guide tube 141 according to the first modification example is blocked by the tampon main body 20. In this state, the guide tube 141 according to the first modification example is connected to the outer cylinder 40 and the air suction device 144 operates. Here, when assuming that the airhole 141k is not provided, the air suction device 144 only reduces pressure inside the guide tube 141 according to the first modification example and does not generate the air flow.

On the other hand, in the case where the airhole 141k is provided, the air flows into the guide tube 141 through the airhole 141k and thus forementioned air flow is generated. Thereby in the case where the tampon main body 20 inserted into the guide tube 141 according to the first modification example is inserted into the outer cylinder 40, the cord 22 of the tampon main body 20 extends straightly by air suction of the air suction device 144. As a result, the tampon main body 20 inserted into the guide tube 141 according to the first modification example is inserted properly into the outer cylinder 40 from the side including the cord 22.

<<Regarding Second Modification Example>>

In above explanation, the configuration for inserting the leading-end part of the outer cylinder 40 into the guide tube 141 is explained. However, in the second modification example, as shown in FIGS. 17A and 17B, a one end part in the longitudinal direction of a guide tube 141 is inserted into the leading-end part of the outer cylinder 40 from the leading-end opening 43 of the outer cylinder 40. That is, the guide tube 141 according to the second modification example is connected to the outer cylinder 40 by inserting its one end part in the longitudinal direction into the leading-end part of the outer cylinder 40.

In detail, as shown in FIGS. 17A and 17B, the guide tube 141 according to the second modification example includes, at the one end part in the longitudinal direction, an outer cylindrical part 141p that has an inner diameter slightly larger than the external diameter of the outer cylinder 40, and an inner cylindrical part 141q positioned at inner side of the outer cylindrical part 141p and having an external diameter that gets larger from one end to other end. And a ring-shaped gap 141r is formed between the outer cylindrical part 141p and the inner cylindrical part 141q.

And the guide tube 141 according to the second modification example will be in a state where the inner cylindrical part 141q is inserted into the leading-end part of the outer cylinder 40 by moving towards the outer cylinder 40 on which the bending process has been performed by the bending mechanism 150. Thereby, the guide tube 141 according to the second modification example contacts the inner wall surface of the petaloid part 44 at an outer peripheral surface of the inner cylindrical part 141q and thus connects to the outer cylinder 40. Further, as shown in FIG. 17B, in the case where the guide tube 141 according to the second modification example and the outer cylinder 40 are connected, each of the petaloid parts 44 will be in a state of being sandwiched between the outer cylindrical part 141p and the inner cylindrical part 141q in the gap 141r.

As above, in the configuration of the second modification example, the drive section 142 moves the guide tube 141 towards the outer cylinder 40 on which the bending process is performed and inserts the one end part in the longitudinal direction of the guide tube 141 from the leading-end opening 43 into the outer cylinder 40, and thus contacts the one end part in the longitudinal direction of the guide tube 141 with the leading-end part of the outer cylinder 40 and connects the guide tube 141 and the outer cylinder 40. In such configuration, it is possible to smoothly connect the guide tube 141 and the outer cylinder 40. And the petaloid part 44 of the outer cylinder 40 contacts the outer peripheral surface of the one end part in the longitudinal direction of the guide tube 141 (specifically, inner cylindrical part 141q) and thus the tampon main body 20 inserted into the guide tube 141 is inserted properly into the outer cylinder 40 without the cord 22 being caught by the petaloid part 44.

Also, as shown in FIG. 17A, above airhole 141k is formed at one end side in the longitudinal direction of an outer peripheral part 141h of the guide tube 141 according to the second modification example. The reason why the airhole 141k is included is mentioned above.

Figure 18:
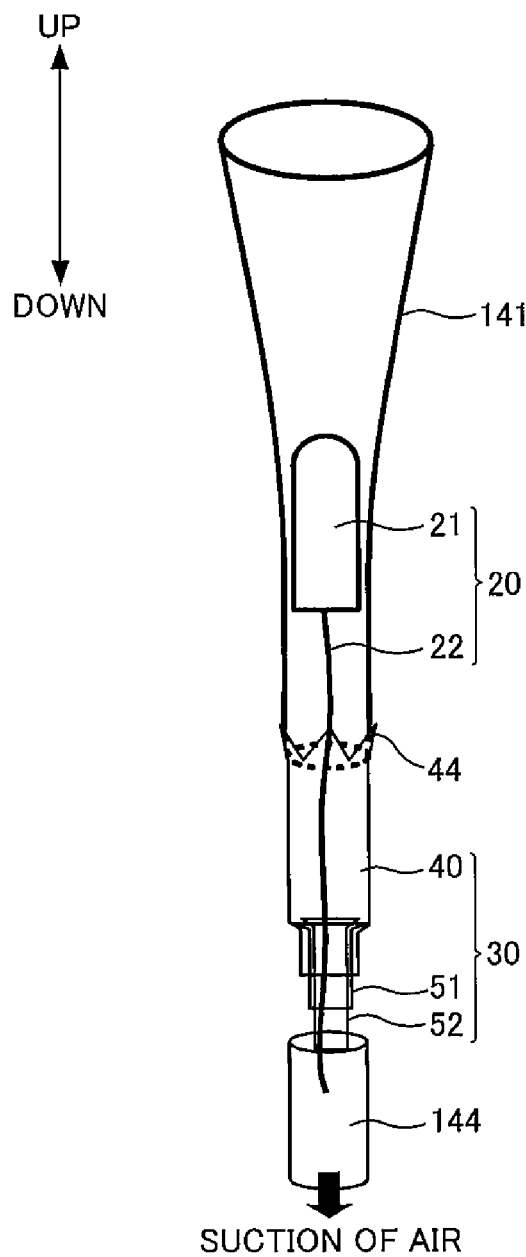
FIG. 18 is a diagram showing other structure for inserting one end part of the guide tube 141 in the longitudinal direction into a leading end part of the outer cylinder 40.

Further, the configuration of which the one end part in the longitudinal direction of the guide tube 141 is inserted into the leading-end part of the outer cylinder 40 from the leading-end opening 43 of the outer cylinder 40 is not limited to the configuration shown in FIGS. 17A and 17B. For example, the configuration shown in FIG. 18 may be possible. That is, as shown in FIG. 18, it is possible that the one end part in the longitudinal direction of the guide tube 141 has a simple cylindrical shape, and the guide tube 141 and the outer cylinder 40 are connected by inserting the one end part into the leading-end part of the outer cylinder 40 on which the bending process is performed. FIG. 18 is a diagram showing other structure for inserting the one end part in the longitudinal direction of the guide tube 141 into the leading-end part of the outer cylinder 40.

Other Embodiment

In the above-mentioned various embodiments, the manufacturing apparatus and the method of manufacturing the tampon 10 (assembling apparatus 100) of the present invention have been mainly discussed. However, the above-mentioned embodiments are provided for the purpose of facilitating the understanding of the present invention only and do not give any limitation to the present invention. It goes without saying that any modifications and improvements to the present invention can be made without departing from the spirit of the invention and the present invention includes its equivalents. Further, the above-mentioned setting values, dimensional values, and shapes etc. are merely examples to show effectiveness of the present invention and should not be understood as any limitation to the present invention.

Also, in the above embodiment, the tampon 10 including the extendable inner cylinder 50 with two-tier structure as pushing member is described. However there is no limitation to this. For example, the tampon 10 including the inner cylinder 50 of fixed length (not extendable) is possible.

Also, in the above embodiment, the outer cylinder 40 is mounted on the mount 160 while the leading-end opening 43 is facing substantially directly upward (in a state of being stand-up). And the drive section 142 lowers the guide tube 141 toward the outer cylinder 40 in the case where the outer cylinder 40 is transported to the lower position of the guide tube 141. That is, in the above embodiment, the configuration in which the guide tube 141 and the outer cylinder 40 are connected along the vertical direction, and the tampon main body 20 is inserted into the outer cylinder 40 from upside is described. However, there is no limitation to this and the outer cylinder 40 can be mounted on the transport conveyor 110 while the leading-end opening 43 is substantially facing its side (in a state of lying on its side). In such configuration, the drive section 142 moves the guide tube 141 towards the outer cylinder 40 from the side of the outer cylinder 40 and connects the guide tube 141 and the outer cylinder 40 along the horizontal direction. And the tampon main body 20 inserted into the guide tube 141 is inserted into the outer cylinder 40 from the side of the outer cylinder 40.

Also, the configuration of connecting the guide tube 141 and the outer cylinder 40 is not limited to the configuration of moving the guide tube 141 towards the outer cylinder 40. The drive section 142 can connect the guide tube 141 and the outer cylinder 40 by moving one of the guide tube 141 and the outer cylinder 40 toward the other, and thus contact the guide tube 141 to the leading-end part of the outer cylinder 40. Therefore, the guide tube 141 and the outer cylinder 40 can be connected by moving the outer cylinder 40 towards the guide tube 141.

REFERENCE SIGNS LIST

10 tampon, 20 tampon main body, 21 cotton body, 22 cord, 30 applicator, 40 outer cylinder (accommodating cylinder), 41 major diameter part, 42 minor diameter part, 43 leading-end opening, 44 petaloid part, 45 rear-end opening, 46 annular rib, 47 stepped part, 50 inner cylinder (pushing member), 51 first inner cylinder, 51a flange part, 51b annular protrusion, 52 second inner cylinder, 52a flange part, 52b protruded part, 52c flared part, 100 assembling apparatus (apparatus for manufacturing tampon 10), 110 transport conveyor, 120 outer cylinder supplying mechanism, 121 outer cylinder feeder, 121a vibratory table, 122 transport path, 122a accumulating part, 122b drop chute, 122c accumulating part, 130 inner cylinder inserting mechanism (pushing member inserting mechanism), 131 first inner cylinder inserting mechanism, 132 second inner cylinder inserting mechanism, 133 inner cylinder feeder, 133a vibratory table, 133b rail, 134 tube, 135 inner cylinder pressing part, 135a pressing member, 140 tampon main body inserting mechanism, 141 guide tube, 141a tapered part, 141b cylindrical part, 141c broadened part, 141d first cylindrical part, 141e second cylindrical part, 141f stopper, 141g rotation axis, 141h outer peripheral part, 141i approach hole, 141j constricted part, 141k airhole, 141p outer cylindrical part, 141q inner cylindrical part, 141r gap, 142 drive section, 143 tampon main body pressing part (pressing part), 143a pressing jig, 144 air suction device, 145 support member, 150 bending mechanism, 151 first pusher unit, 152 second pusher unit, 153 third pusher unit, 154 pusher, 154a tapered part, 154b disk part, 155 auxiliary pusher, 160 mount, 200 other tampon main body inserting mechanism, 201 holder, 201a throughhole, 202 other tampon main body pressing part, 202a pressing jig

The invention claimed is:

1. An apparatus for manufacturing a tampon, the tampon including a tampon main body having a cord, an accommodating cylinder accommodating the tampon main body, a pushing member movable inside the accommodating cylinder for pushing the tampon main body out of the accommodating cylinder, a leading-end part of the accommodating cylinder including a plurality of petaloid parts surrounding a leading-end opening of the accommodating cylinder, the tampon main body being formed by heating after pressing a cotton strip, said apparatus comprising:
 a pushing-member inserting mechanism configured to insert the pushing member into the accommodating cylinder through the leading-end opening;
 a first tampon main body inserting mechanism configured to insert the tampon main body into the accommodating cylinder, from a side including the cord, through the leading-end opening,
 the first tampon main body inserting mechanism including:
  a guide tube having an upper-end opening and a lower-end opening, and configured to guide the tampon main body inserted into the guide tube;
  a drive section configured to cause the guide tube and the accommodating cylinder to be connected by moving one of the guide tube and the accommodating cylinder towards the other and thus causing the guide tube to contact the leading-end part of the accommodating cylinder;
  a pressing part configured to press the tampon main body inserted into the guide tube so as to insert the tampon main body into the accommodating cylinder connected to the guide tube; and
  an air suction device configured to suck air from a rear-end side of the accommodating cylinder when the tampon main body is inserted into the accommodating cylinder,
  wherein the guide tube includes an air hole at an outer peripheral part of the guide tube and between the upper-end opening and the lower-end opening; and
 a bending mechanism configured to bend each of the plurality of petaloid parts outwardly in a radial direction of the accommodating cylinder in a bending process,
 wherein
 the guide tube includes
  a tapered part provided in a first end part of the guide tube in a longitudinal direction of the guide tube, wherein an internal diameter of the tapered part becomes smaller from the first end part of the guide tube toward a second end part of the guide tube; and
  a cylindrical part adjacent to the tapered part at an end side of the tapered part in the longitudinal direction of the guide tube,
 the drive section is configured to move the guide tube toward the accommodating cylinder on which the bending process is performed, and insert the accommodating cylinder into the guide tube from one end side in the longitudinal direction of the guide tube, and
 the guide tube is configured to guide the leading-end part of the accommodating cylinder into the cylindrical part to cause a leading end of the corresponding petaloid part to contact with an inner peripheral surface of the tapered part, and fit the leading-end part into the cylindrical part so as to cause the petaloid part to contact with an inner peripheral surface of the cylindrical part, whereby the guide tube is connected to the accommodating cylinder.

2. The apparatus according to claim 1, further comprising:
 a second tampon main body inserting mechanism configured to insert the tampon main body into the guide tube, wherein
 the drive section is configured to connect the guide tube and the accommodating cylinder by moving the guide tube, while the tampon main body is held by the second tampon main body inserting mechanism, towards the accommodating cylinder and thus causing the guide tube to contact with the leading-end part of the accommodating cylinder, and
 a length of the guide tube in the longitudinal direction thereof is longer than a length from a leading end to a rear end of the tampon main body in a state where the cord is extended.

3. The apparatus according to claim 2, wherein,
 the guide tube is held in a state where the longitudinal direction of the guide tube is lying along a vertical direction, and
 the second tampon main body inserting mechanism is configured to insert the tampon main body from another side, opposite to the side including the cord, into the guide tube from a downside of the guide tube in the vertical direction.

4. The apparatus according to claim 1, wherein,
 the cylindrical part includes a first cylindrical part and a second cylindrical part between the first cylindrical part and the tapered part in the longitudinal direction of the guide tube,
 the pressing part is configured to press the tampon main body to move inside the first cylindrical part,
 the guide tube is configured to be connected to the accommodating cylinder by fitting the leading-end part of the accommodating cylinder into the second cylindrical part such that the petaloid part is in contact with an inner peripheral surface of the second cylindrical part, and
 when the leading-end part is fitted into the second cylindrical part, an inner peripheral surface of the first cylindrical part is positioned inward of the petaloid part contacting the inner peripheral surface of the second cylindrical part in the radial direction of the guide tube.

5. An apparatus for manufacturing a tampon, the tampon including
- a tampon main body having a cord side with a cord,
- an accommodating cylinder accommodating the tampon main body, the accommodating cylinder including, in a leading-end part thereof, a plurality of petaloid parts surrounding a leading-end opening of the accommodating cylinder, and
- a pushing member disposed inside the accommodating cylinder for pushing the tampon main body out of the accommodating cylinder, said apparatus comprising:
- a pushing-member inserting mechanism configured to insert the pushing member into the accommodating cylinder through the leading-end opening; and
- a first tampon main body inserting mechanism configured to insert the tampon main body into the accommodating cylinder, from the cord side, through the leading-end opening,
  - the first tampon main body inserting mechanism including:
    - a guide tube configured to cooperate with both the tampon main body and the accommodating cylinder so as to guide the tampon main body into the accommodating cylinder;
    - a drive section configured to cause one of the guide tube and the accommodating cylinder to move towards the other so as to cause the guide tube to contact with the leading-end part of the accommodating cylinder;
    - a pressing part configured to press the tampon main body inside the guide tube into the accommodating cylinder connected to the guide tube; and
    - an air suction device configured to suck air from a rear-end side of the accommodating cylinder when the tampon main body is inserted into the accommodating cylinder, and
  - a bending mechanism configured to bend each of the plurality of petaloid parts outwardly in a radial direction of the accommodating cylinder in a bending process,
wherein
the guide tube includes
  - a tapered part provided in a first end part of the guide tube in a longitudinal direction of the guide tube, wherein an internal diameter of the tapered part becomes smaller from the first end part of the guide tube toward a second end part of the guide tube; and
  - a cylindrical part adjacent to the tapered part at an end side of the tapered part in the longitudinal direction of the guide tube,
the drive section is configured to move the guide tube toward the accommodating cylinder on which the bending process is performed, and insert the accommodating cylinder into the guide tube from one end side in the longitudinal direction of the guide tube, and
the guide tube is configured to guide the leading-end part of the accommodating cylinder into the cylindrical part to cause a leading end of the corresponding petaloid part to contact with an inner peripheral surface of the tapered part, and fit the leading-end part into the cylindrical part so as to cause the petaloid part to contact with an inner peripheral surface of the cylindrical part, whereby the guide tube is connected to the accommodating cylinder.

6. The apparatus according to claim 5, further comprising:
a second tampon main body inserting mechanism configured to insert the tampon main body into the guide tube,
wherein
the second tampon main body inserting mechanism is disposed below the guide tube in a vertical direction, and
the second tampon main body inserting mechanism is configured to insert the tampon main body, from a cotton body side opposite to the cord side of the tampon main body, into the guide tube.

7. The apparatus according to claim 6, wherein the drive section is configured to move the guide tube towards the accommodating cylinder while the tampon main body is held by the second tampon main body inserting mechanism.

8. The apparatus according to claim 6, wherein the guide tube comprises a stopper configured to hold the tampon main body, which is inserted into the guide tube by the second tampon main body inserting mechanism, inside the guide tube.

9. The apparatus according to claim 6, wherein the guide tube is disposed in a state where the longitudinal direction of the guide tube aligns with the vertical direction.

10. The apparatus according to claim 5, wherein the guide tube further comprises a broadened part at the second end part, the broadened part has an internal diameter greater than an internal diameter of the cylindrical part, and the guide tube is configured to receive the tampon main body from the broadened part.

11. The apparatus according to claim 5, wherein
the cylindrical part comprises a first cylindrical part and a second cylindrical part having an internal diameter larger than the first cylindrical part, and
the second cylindrical part is configured to directly contact the leading-end part of the accommodating cylinder when the guide tube receives the accommodating cylinder.

12. The apparatus according to claim 5, wherein a length of the guide tube in the longitudinal direction thereof is longer than a length from a leading end to a rear end of the tampon main body in a state where the cord is extended.

13. The apparatus according to claim 5, wherein
the guide tube has an upper-end opening and a lower-end opening opposite to the upper end opening in the longitudinal direction of the guide tube, and
the guide tube further includes an air hole at an outer peripheral part of the guide tube and between the upper-end opening and the lower-end opening.

\* \* \* \* \*